US011826031B2

(12) United States Patent
Considine et al.

(10) Patent No.: US 11,826,031 B2
(45) Date of Patent: Nov. 28, 2023

(54) SURGICAL RETRACTORS AND METHODS OF USING THE SAME

(71) Applicant: Alphatec Spine, Inc., Carlsbad, CA (US)

(72) Inventors: David Considine, Carlsbad, CA (US); James Lee, Vista, CA (US); Andrew W. Rajek, Escondido, CA (US); Max C. Zemezonak, San Diego, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 17/546,045

(22) Filed: Dec. 8, 2021

(65) Prior Publication Data
US 2022/0175362 A1 Jun. 9, 2022

Related U.S. Application Data

(60) Provisional application No. 63/123,394, filed on Dec. 9, 2020.

(51) Int. Cl.
*A61B 17/02* (2006.01)
*A61B 17/70* (2006.01)

(52) U.S. Cl.
CPC ........ *A61B 17/0206* (2013.01); *A61B 17/025* (2013.01); *A61B 17/7074* (2013.01); *A61B 2017/0256* (2013.01)

(58) Field of Classification Search
CPC . A61B 17/02; A61B 17/0206; A61B 17/0218; A61B 17/025; A61B 2017/0256; A61B 2017/0262
See application file for complete search history.

(56) References Cited

U.S. PATENT DOCUMENTS

| 6,929,606 B2 | 8/2005 | Ritland |
| 7,758,584 B2 | 7/2010 | Bankoski |

(Continued)

FOREIGN PATENT DOCUMENTS

| WO | 2004/047650 | 11/2003 |
| WO | 2006/017886 | 2/2006 |

(Continued)

OTHER PUBLICATIONS

Written Opinion of the International Searching Authority, International Application No. PCT/US2021/062455, dated Jun. 22, 2023.

*Primary Examiner* — Julianna N Harvey
*Assistant Examiner* — Angel Roberto Mora-Velazquez
(74) *Attorney, Agent, or Firm* — Robert Winn

(57) ABSTRACT

A retractor assembly that includes a base portion in slidable engagement with two or more retractor arms with at least one of the retractor arms releasably securing a retractor blade configured to be anchored to a bone anchor. The retractor blade includes an elongate blade portion with a retractor engagement portion positioned at the proximal end of the elongate blade portion and an anchor mechanism positioned at the distal end of the elongate blade portion. The anchor mechanism includes a first jaw and second jaw configured to engage the bone implant. When closed around or anchored to the bone implant—which may be a shank of a modular screw system—the components of the modular screw are able to be assembled to the shank without adjusting, loosening, or opening the anchor mechanism.

29 Claims, 11 Drawing Sheets

(56) References Cited

U.S. PATENT DOCUMENTS

| | | | |
|---|---|---|---|
| 8,357,184 | B2 | 1/2013 | Woolley |
| 8,435,269 | B2 | 5/2013 | Woolley |
| 8,535,320 | B2 | 9/2013 | Woolley |
| 8,636,655 | B1 | 1/2014 | Childs |
| 8,979,749 | B2 | 3/2015 | Gorek |
| 9,050,146 | B2 | 6/2015 | Woolley |
| 9,216,016 | B2 | 12/2015 | Fletcher |
| 9,307,972 | B2 | 4/2016 | Lovell |
| 9,414,828 | B2 | 8/2016 | Abidin |
| 9,622,795 | B2 | 4/2017 | Reitblat |
| 9,675,337 | B2 | 6/2017 | Gorek |
| 9,700,293 | B2 | 7/2017 | Cryder |
| 9,795,370 | B2 | 10/2017 | O'Connell |
| 9,795,417 | B2 | 10/2017 | Beger |
| 9,962,147 | B2 | 5/2018 | O'Connell |
| 9,980,712 | B2 | 5/2018 | Seex |
| 10,092,283 | B2 | 10/2018 | Cryder |
| 10,172,652 | B2 | 1/2019 | Woolley |
| 10,231,724 | B1 | 3/2019 | Lovell |
| 10,278,687 | B2 | 5/2019 | Cryder |
| 11,116,489 | B2 * | 9/2021 | Kim .................. A61B 17/0206 |
| 2003/0149341 | A1 | 8/2003 | Clifton |
| 2009/0187080 | A1 | 7/2009 | Seex |
| 2011/0301422 | A1 | 12/2011 | Woolley |
| 2014/0031874 | A1 | 1/2014 | Kucharzyk |
| 2015/0313585 | A1 * | 11/2015 | Abidin ................ A61B 17/025 600/219 |
| 2016/0074029 | A1 * | 3/2016 | O'Connell ............ A61B 17/02 600/215 |
| 2016/0081683 | A1 | 3/2016 | Cianfrani |
| 2016/0106408 | A1 | 4/2016 | Ponmudi |
| 2017/0035406 | A1 | 2/2017 | Abidin |
| 2017/0273677 | A1 | 9/2017 | Gorek |
| 2017/0311980 | A1 | 11/2017 | Solitario |
| 2018/0035990 | A1 | 2/2018 | Eftekhar |
| 2018/0153585 | A1 | 6/2018 | Levine |
| 2018/0206833 | A1 | 7/2018 | O'Connell |
| 2018/0228520 | A1 | 8/2018 | Bobbitt |
| 2019/0000438 | A1 | 1/2019 | Cryder |
| 2019/0008498 | A1 | 1/2019 | McClymont |
| 2019/0090979 | A1 | 3/2019 | Medeiros |
| 2019/0110785 | A1 | 4/2019 | Serokosz |
| 2019/0090864 | A1 | 5/2019 | Medeiros |
| 2019/0142480 | A1 | 5/2019 | Wolley |
| 2019/0167446 | A1 | 6/2019 | Conrad |
| 2021/0085307 | A1 * | 3/2021 | Sandham ............. A61B 90/361 |

FOREIGN PATENT DOCUMENTS

| | | |
|---|---|---|
| WO | 2007/121271 | 10/2007 |
| WO | 2011/133160 | 10/2010 |
| WO | 2011/059491 | 11/2010 |
| WO | 2010/135537 | 3/2011 |
| WO | 2015/116624 | 8/2015 |
| WO | 2016/025020 | 2/2016 |
| WO | 2017/031287 | 2/2017 |
| WO | 2018/150214 | 2/2017 |
| WO | 2018/065436 | 10/2017 |
| WO | 2018/087736 | 5/2018 |
| WO | 2018/144988 | 8/2018 |
| WO | 2018/162647 | 9/2018 |
| WO | 2019/058343 | 3/2019 |

* cited by examiner

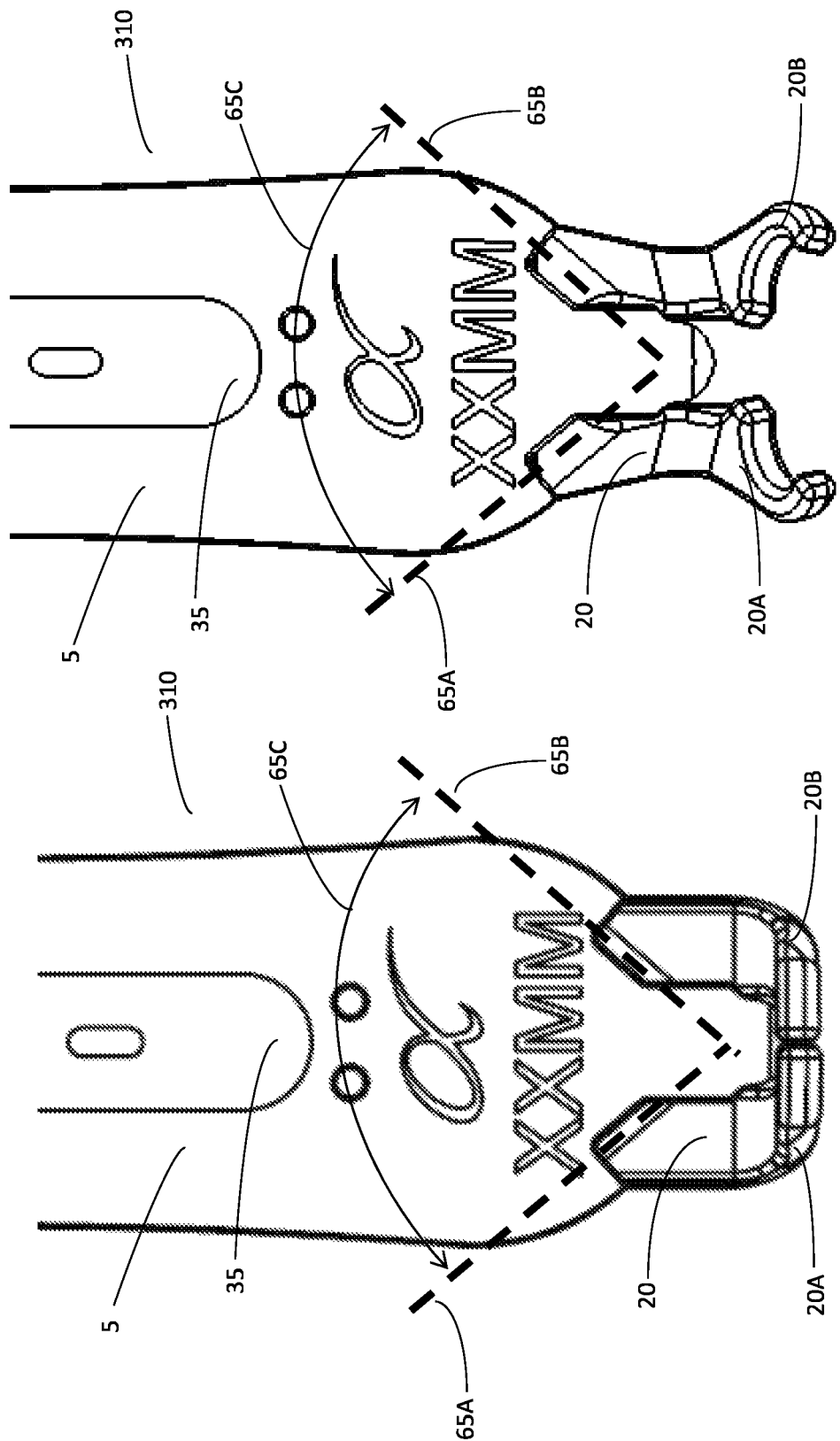

SURGICAL RETRACTORS AND METHODS OF USING THE SAME

CROSS-REFERENCE TO RELATED CASES

This application claims priority to U.S. Provisional Application No. 63/123,394, filed Dec. 9, 2020, the entire contents of which are incorporated herein by reference.

BACKGROUND

The present disclosure relates to surgical retractors configured to provide access to a surgical site, such as a portion of a patient's spine. Also disclosed herein are methods of using such surgical retractors in surgical procedures, such as a spinal surgery.

SUMMARY

Disclosed herein are modular surgical retractors, some of which utilize anchored retractor blades. Such anchored blades include an elongate blade portion, a retractor engagement portion positioned at the proximal end of the elongate blade portion, a first jaw and second jaw positioned at the distal end of the elongate blade portion and configured to engage a bone implant, the first and second jaws configured to occupy a closed configuration and an open configuration, a control assembly configured to transition the first and second jaws between the open configuration and the closed configuration.

According to some embodiments, the elongate blade portion lies substantially in a first plane and a first portion of the first and second jaws—when in the closed configuration—lies in a second plane, the first and second planes transecting each other at an angle of about 65° to about 120°. According to some embodiments, at least a portion of the retractor engagement portion lies in a third plane, the first and third planes transecting each other at an angle of about 65° to about 120. The second and third planes can be substantially parallel. In some embodiments, a second portion of the first and second jaws—when in the closed configuration—lies in the first plane.

According to some embodiments, the first jaw pivots about a first axis and the second jaw pivots about a second axis. The first and second axes may lie in the first plane and may transect each other such that an angle between the first and second axes is from about 55° to about 115°. The first and second axes may be symmetrical relative to the elongate blade portion.

According to some embodiments, the first and/or second jaw includes a base portion and an arcuate portion. The base portion pivotally engages the distal end of the elongate blade portion. The arcuate portion is designed and shaped to engage the bone implant when the first and second jaws are in the closed configuration. The arcuate portion may be sized and shaped to engage a head of a pedicle screw. The first and second jaws may be configured to allow for the assembly of a modular tulip on the head of the pedicle screw when the first and second jaws are in the closed configuration.

According to some embodiments, the control assembly is positioned on the rear face of the elongate blade portion. Positioning the control assembly on the rear portion of the blade may allow a user to access the control assembly while using an instrument—such as a screw driver—on the front portion of the blade.

The control assembly may include a tool engagement portion, a movable block to engage the first and second jaws so as to transition them between the open and closed configurations, and a connection rod mechanically connecting the tool engagement portion and the movable block and configured to translate rotation of the tool engagement portion into movement of the block either distally or proximally along the elongate blade portion. The tool engagement portion may be positioned at the proximal end of the elongate blade portion. In some embodiments, the movable block applies an equal force to both the first and second jaws so as to cause them to move in unison between the open and closed configurations.

According to some embodiments, the retractor engagement portion includes a spherical portion configured to be received by a retractor assembly. The spherical portion may include a pair of lateral extensions configured to allow the anchored blade to rotate relative to a retractor assembly in only a single plane.

Some embodiments disclosed herein are for surgical retractor systems that include a retractor assembly, a support engagement portion, and at least one anchored blade. The retractor assemblies may have a first retractor arm and a second retractor arm, each retractor arm configured to releasably engage a retractor blade. The support engagement portion may be releasably engaged with a support structure. The at least one anchored blade may be any one of the anchored blade embodiments disclosed herein that is releasably engaged with the first retractor arm. Some embodiments further include a second anchored blade that may be any one of the anchored blade embodiments disclosed herein that is releasably engaged with the second retractor arm. Some embodiments further include a medial blade engagement portion configured to releasably engage a medial retractor blade. Such embodiments may also include a medial retractor blade releasably engaged with the medial blade engagement portion of the retractor assembly. The support structure may be secured to a surgical bed or a surgical frame. The support structure may be an A-arm.

Some embodiments disclosed herein relate to methods of securing an anchored blade to a first bone implant. Such methods include, first, positioning a first anchored blade that may be any one of those disclosed herein so that at least a portion of the first and second jaws of the anchored blade is positioned below a top surface of the first bone implant and, second, activating the control assembly of the first anchored blade to transition the first and second jaws from the open configuration to the closed configuration to anchor the first anchored blade to the first bone implant. Some methods further include, first, positioning a second anchored blade that may be any one of those disclosed herein so that at least a portion of the first and second jaws of the second anchored blade is positioned below a top surface of a second bone implant, and, second, activating the control assembly of the second anchored blade to transition the first and second jaws from the open configuration to the closed configuration to anchor the second anchored blade to the second bone implant.

In some embodiments, the first bone implant is secured to a first vertebra prior to the first anchored blade is secured to the first bone implant and/or the second bone implant is secured to a second vertebra prior to the second anchored blade is secured to the second bone implant. In some embodiments, the first bone implant is secured to a first vertebra after the first anchored blade is secured to the first bone implant and/or the second bone implant is secured to a second vertebra after the second anchored blade is secured to the second bone implant. In some embodiments, a driver is secured to the first bone anchor or second bone anchor prior to securing the first or second bone anchor to the first or second vertebra. The first bone implant and/or the second bone implant may be a pedicle screw having a threaded shank portion and a head portion. The head portion may be at least partially spherical in shape. The pedicle screw may be a component of a modular screw assembly. Some methods further include assembling the modular screw assembly after the first and/or second anchored blades have been anchored to the first and/or second bone implants, respectively. Some methods disclosed herein form part of a procedure for transforaminal lumbar interbody fixation.

Also disclosed herein are various embodiments of anchored surgical retractors that include a base portion having first and second extensions and one or more engagement portions, a first retractor arm, a second retractor arm. The first retractor arm has proximal and distal ends and a third receiving area at the proximal end configured to slidably receive the first extension of the base portion and a fourth receiving area at the distal end configured to releasably engage a portion of a first retractor blade. The second retractor arm has proximal and distal ends and a fifth receiving area at the proximal end configured to slidably receive the second extension of the base portion and a sixth receiving area at the distal end configured to releasably engage a portion of a second retractor blade. In some embodiments, the medial, first, and second retractor blades together create an adjustable surgical corridor, though, in some embodiments, only two of the three retractor blades are used to create the adjustable surgical corridor.

According to some embodiments, the first and/or second retractor blades include an elongate blade portion having a proximal end and a distal end, a retractor engagement portion positioned at the proximal end of the elongate blade portion, and an anchor mechanism positioned at the distal end of the elongate blade portion. In some embodiments, the anchor mechanism includes a first jaw and a second jaw configured to engage a bone implant—the first and second jaws configured to transition between a closed configuration and an open configuration. In the open configuration, a portion of the bone implant is able to pass through the first and second jaws.

According to some embodiments, the first and second retractor blades include a control assembly configured to transition the first and second jaws between the open configuration and the closed configuration. In some cases, the base portion further comprises a first receiving area and the retractor assembly further comprises a medial retractor arm with proximal and distal ends. The medial retractor arm may have a second receiving area at the distal end designed and configured to releasably engage a portion of a medial retractor blade. The proximal end may be configured to be slidably received in the first receiving area of the base portion.

Some embodiments of a retractor assembly further include a lateral retractor arm having a proximal end and a distal end with the proximal end having a seventh receiving area configured to releasably engage a lateral arm engagement portion located on one of the first retractor arm or second retractor arm. The distal end may include an eighth receiving area configured to releasably engage a portion of a lateral retractor blade.

In some embodiments, the first and/or second retractor blade is as described elsewhere herein. In some embodiments, both the first and second retractor blades is as described elsewhere herein.

These and other features are disclosed in greater detail in the accompanying figures and the Detailed Description below.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings wherein like structure is indicated with like reference numerals and in which:

FIGS. 8A & 8B are partial, frontal plan views of the anchored blade of FIG. 7 with the anchoring assembly in a closed configuration (FIG. 8A) and an open configuration (FIG. 8B);

DETAILED DESCRIPTION

The present disclosure relates to surgical retractors and specifically to retractors configured for use in spinal surgery. The retractor assemblies disclosed herein benefit from retractor blades that are easily attached to and removed from the retractor arms of the assembly, the ability to use no more than two retractor blades in some embodiments while using at least four retractor blades in some embodiments, the ability to anchor at least one and/or two retractor blades to a fixation element, and the ability to assemble a modular screw even as that same screw serves as an anchor for the anchored retractor. These and other benefits will be apparent to a skilled artisan based on the present disclosure.

Figure 1:
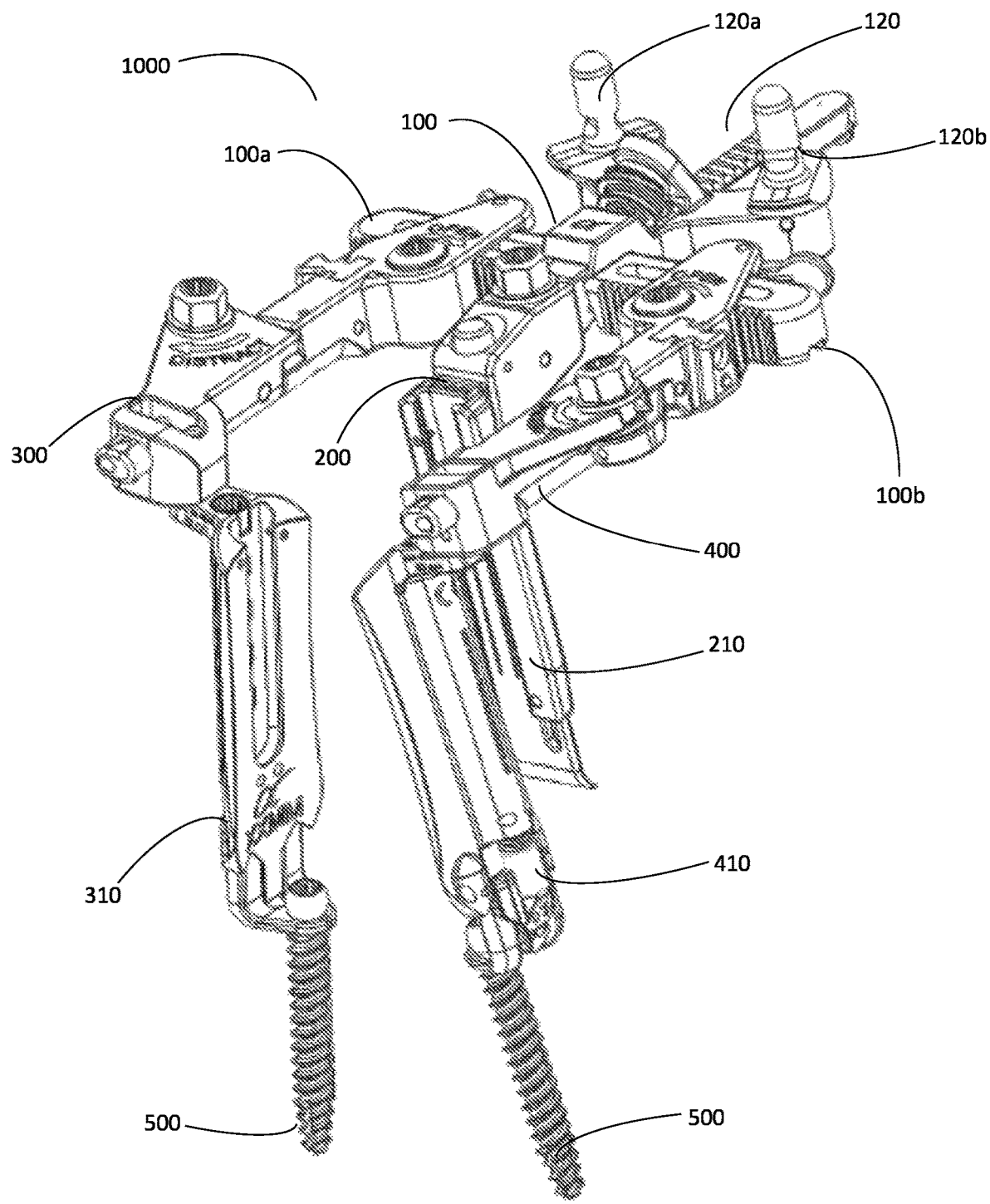
FIG. 1 is a perspective view of a surgical retractor according to the present disclosure.

FIG. 1 illustrates one embodiment of a surgical retractor 1000. In this illustrated embodiment, retractor 1000 includes a base portion 100 having two lateral extensions 110a and 110b. Extensions 110a and 110b are illustrated as extending in opposite directions so as to form a substantially straight line. In some embodiments, extensions 110a and 110b are positioned relative to each other to form an angle that may be acute or obtuse. Such variations in the orientation may facilitate certain procedures or approaches.

Base portion 100 further includes an engagement portion 120 positioned posteriorly on base portion 100. In this illustrated embodiment, engagement portion 120 includes two engagement extensions 120a and 120b configured for attachment to a support structure, such as an A-arm (not illustrated). The presence of two engagement extensions allows a user to vary the position of retractor 1000 relative to the support structure and/or the position of the support structure relative to retractor 1000 and/or relative to the surgical site.

In the illustrated embodiment of FIG. 1, retractor 1000 includes three retractor arms—medial retractor arm 200 and two retractor arms 300 and 400 that have attached to them anchored retractor blades 310 and 410, respectively. Medial arm 200 has attached to it medial blade 210. As will be discussed in greater detail below, each of these blades are easily attached to base portion 100 during a surgical procedure and may be easily removed from their respective retractor arms during the procedure. Further, each retractor arm may be removed from base portion 110 to allow for maximum customizability.

Anchored retractor blades 310 and 410 are each configured to engage or to be anchored to an anchor 500, such as a bone screw or a pedicle screw. In some embodiments, the anchor is a modular pedicle screw, and one or both of anchored retractor blades 310 and 410 is configured to allow for assembly of the modular pedicle screw, which may include the placement of a tulip onto the modular pedicle screw. Such assembly of the tulip onto the modular pedicle screw may be achieved without making any adjustments to anchored retractor blades 310 and 410. For example, anchored retractor blades 310 and 410 need not be removed from the head of the modular pedicle screw let alone loosened from the head to allow for the tulip to be secured to the head of the modular pedicle screw.

According to some embodiments, a method of using retractor 1000 includes a first step of placing one or more bone anchors, such as pedicle screws, in a patient's space. The one or more bone anchors may be modular screws that, during this first step, include just the shank portion of the screw. First retractor blade 310 is then advanced toward a first bone anchor, and the anchor portion of the blade 310 is advanced over a proximal end of the screw. The anchor portion is then closed around the screw. If a second bone anchor is used, retractor blade 410 is advanced toward and anchored onto the second bone anchor in a similar manner as the first retractor blade 310. The respective retractor blades are then secured to a retractor assembly 1000 that includes base portion 100 and retractor arms 300 and 400. The arms may then be manipulated to enlarge an opening that allows access to the patient's spine and, in particular, to an intervertebral space. When sufficient access is achieved, a surgeon may perform any number of procedures, such as a laminectomy or an intervertebral fusion that requires the whole or partial removal of the patient's intervertebral disc and the implantation of an interbody between respective vertebrae.

During or after the above procedures, retractor 1000 may be manipulated to open and/or adjust the configuration of the intervertebral disc space by adjusting the position and/or angulation of retractor blades 310 and 410.

The opening created by retractor 1000 may be further enhanced by the use of medial retractor blade 310 or a lateral retractor blade that is discussed further below.

In some embodiments, retractor 1000 includes only one anchored retractor blade 310 or 410 and one medial blade 210. In some embodiments, retractor 1000 includes anchored retractor blades 310 and 410 and no medial blade 210.

Figure 2:
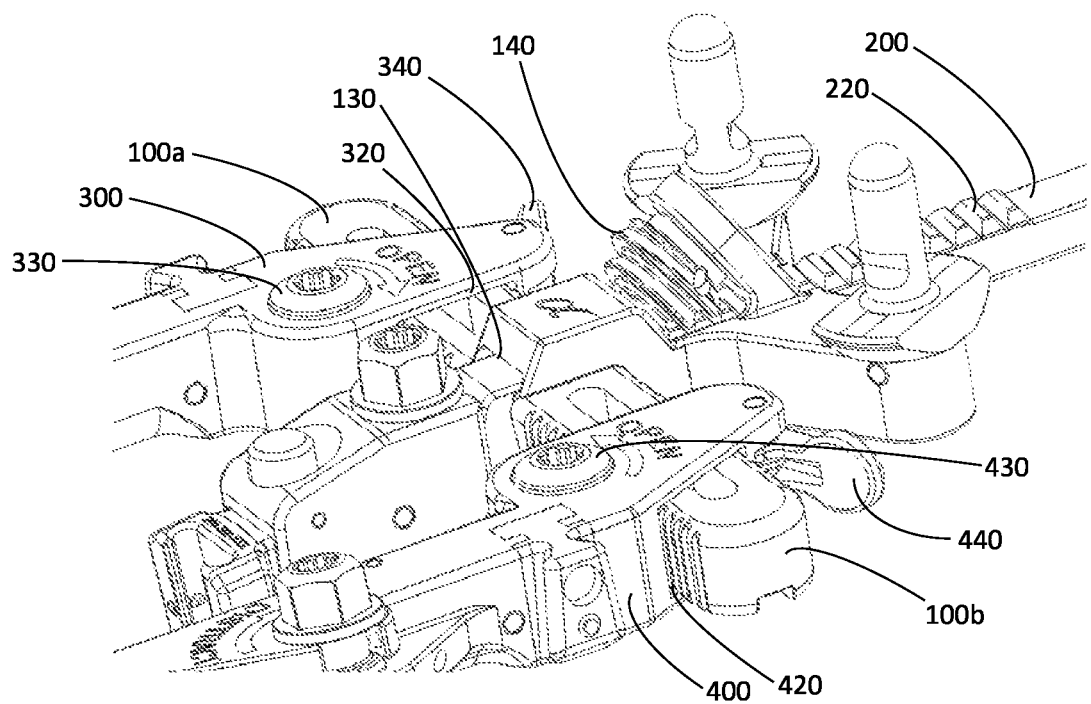
FIG. 2 is an enlarged, perspective view of the embodiment shown in FIG. 1.

FIG. 2 illustrates an enlarged view of retractor 1000 highlighting the engagement of retractor arm 300 with extension 110a of base 100, which is achieved by inserting extension 110a through receiving portion or window 320 of retractor arm 300. Similarly, retractor arm 400 engages with extension 110b by receiving extension 110b through window 420 of retractor arm 400. In contrast, medial arm 200 engages with base 100 by being inserted into a receiving portion on base 100, which is window 130.

Extensions 110a and 110b each include two sets of linear gear teeth. One set of gear teeth on each extension engages with a pinion gear found in each retractor arm to form a rack and pinion mechanism that allows for controlled translation of retractor arms 300 and 400 linearly along extensions 110a and 110b, respectively. Rotation of each respective pinion gear is achieved by rotating expansion mechanisms 330 and/or 430, respectively. In this illustrated embodiment, rotation of either expansion mechanism may be performed only in one direction, the direction of expansion, which is away from medial retractor blade 200, also referred to herein as the midline. This is because each rack and pinion mechanism is coupled with a catch 340 and 440, respectively, that engages the other set of linear gear teeth on each extension. As each expansion mechanism is rotated, each pinion gear rotates and engages with its respective set of linear gear teeth to translate each respective retractor arm away from the midline. As each retractor arm advances, catch 340 and/or catch 440—each of which is spring loaded to maintain engagement with the second set of linear gear teeth—allows each retractor arm to translate away from the midline but prevents either retractor arm from translating back toward the midline. To achieve translation toward the midline, catch 340 and/or catch 440 must be pivoted away from the linear gear teeth thereby allowing the respective retractor arm to translate freely along extension 110a and/or 110b.

In some embodiments, no such catch is used, and translation away from and toward the midline is achieved simply by rotating expansion mechanisms 330 and/or 430, which in some embodiments are modified to require more torque to achieve translation. Requiring higher torque may prevent the expansion mechanisms from being unintentionally rotated by just the forces applied to retractor arms 300 and/or 400.

FIG. 2 also illustrates that medial retractor arm 200 includes a set of linear gear teeth 220 that are configured to engage an adjustment mechanism 140, which in this embodiment is a worm gear, on base portion 100. Depending on the direction it is rotated, rotation of adjustment mechanism 140 causes linear translation of medial retractor arm 200 either away from or toward the surgical corridor created between anchored retractor blades 310 and 410 and medial retractor blade 210.

Figure 3:
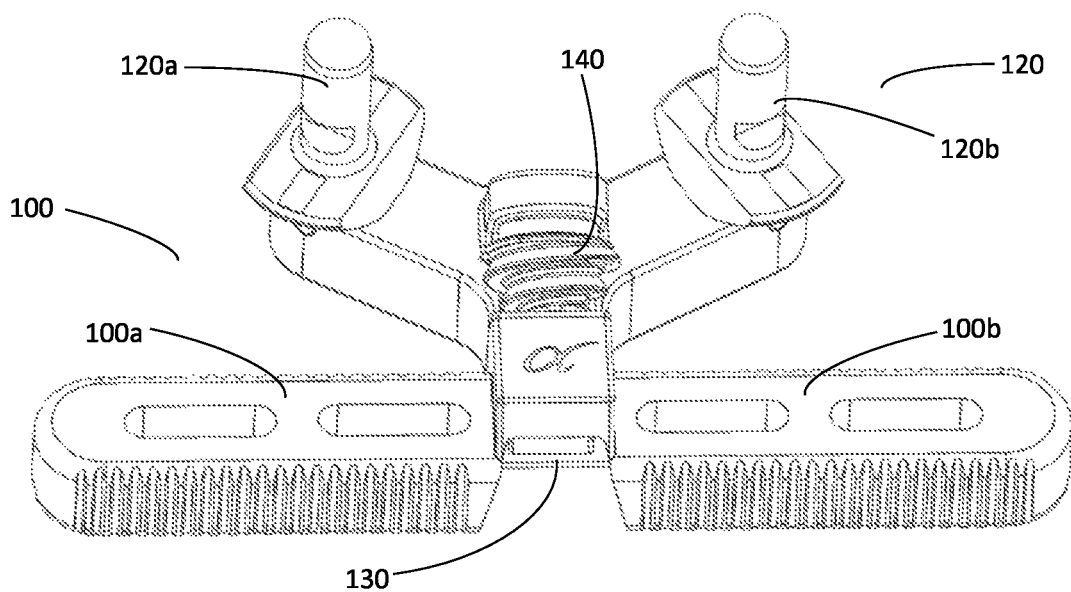
FIG. 3 is a perspective view of a retractor base portion, which is a component of the surgical retractor shown in FIG. 1.

FIG. 3 illustrates base portion 100 without any retractor arms attached. This view clearly illustrates the respective sets of linear gear teeth on each of extension 110a and extension 110b. Also clearly illustrated are the respective engagement extensions 120a and 120b that form engagement portion 120. This embodiment of retractor 1000 includes both engagement extensions 120a and 120b, some embodiments of retractor 1000 may include only one engagement extension. When using retractor 1000, a user may secure retractor 1000 to a surgical table by attaching an A-arm or similar device to either engagement extension 120a or 120b or both. The presence of two engagement extensions provides the user with a variety of engagement orientations to choose from. For example, when approaching a patient's spine from one side of the patient, a particular engagement extension may be the more desirable point of fixation for an A-arm. However, when approaching the patient's spine from the other side, the other engagement extension allows the surgeon to achieve a mirror image of the orientation achieved on the first side of the patient. Or is some cases, a different point of fixation may prove more beneficial if a surgeon is left-handed or vice versa.

Figure 4:
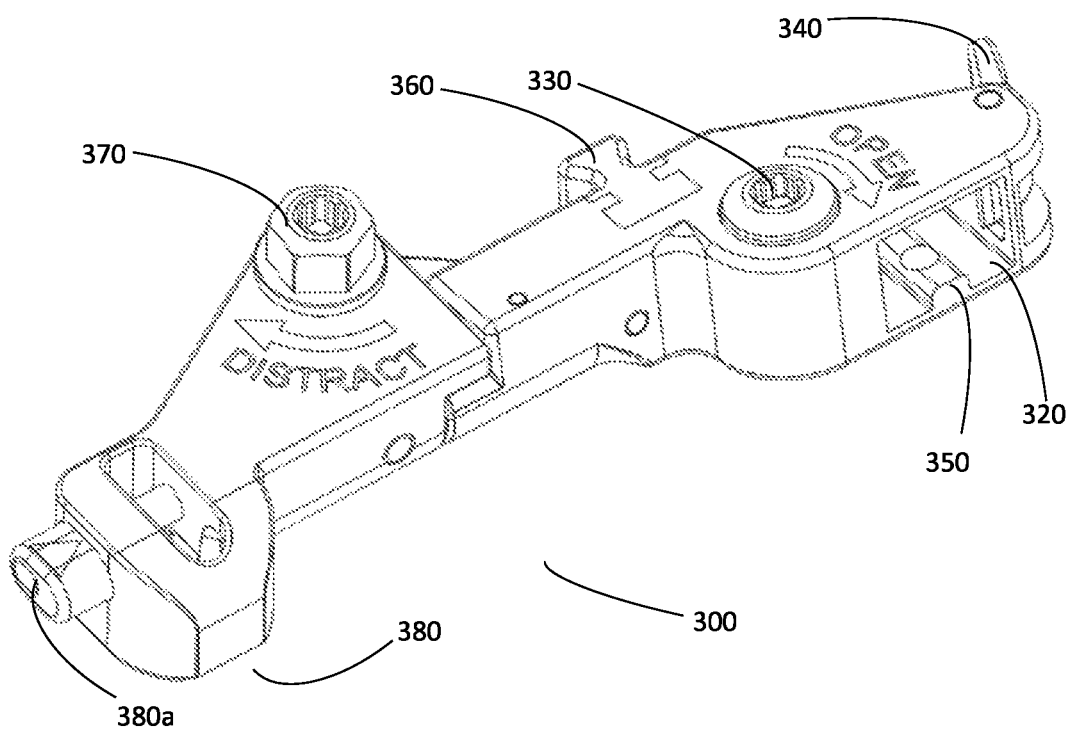
FIG. 4 is a perspective view of a first retractor arm, which is a component of the surgical retractor shown in FIG. 1.

FIG. 4 is a perspective view of retractor arm 300 without base portion 100 or retractor blade 310. This view clearly illustrates receiving portion 320, which, in this illustrated embodiment, includes a raised or keyed portion 350 that engages with a corresponding channel on the underside of extension 110a (not illustrated) to ensure a solid engagement between retractor arm 300 and extension 110a.

Retractor arm 300 also includes auxiliary attachment portion 360 that is configured to serve as a point of attachment for an auxiliary or lateral retractor arm, which is discussed below with reference to FIG. 17.

Retractor arm 300 further includes a distraction mechanism 370 that, when rotated, toes out the distal end of retractor blade 310, thereby allowing for or causing distraction of the vertebrae to which retractor 1000 is attached or anchored.

At its distal end, retractor arm 300 includes a retractor blade engagement portion 380 that is configured to releasably secure a proximal end of retractor blade 310 as discussed below with reference to FIGS. 6 and 7. Retractor blade engagement portion 380 includes a release button 380a that when depressed, allows the proximal end of retractor blade 310 to be released from retractor blade engagement portion 380. However, engaging retractor blade 310 with retractor blade engagement portion 380 does not require the depression of button 380a because the mechanism—discussed in greater detail with respect to FIG. 6—is a passive mechanism that allows for the easy attachment of retractor blade 310 with minimal effort. Engagement of blade 310 with arm 300 simply requires pushing the proximal end of blade 310 into blade engagement portion 380.

Figure 5:
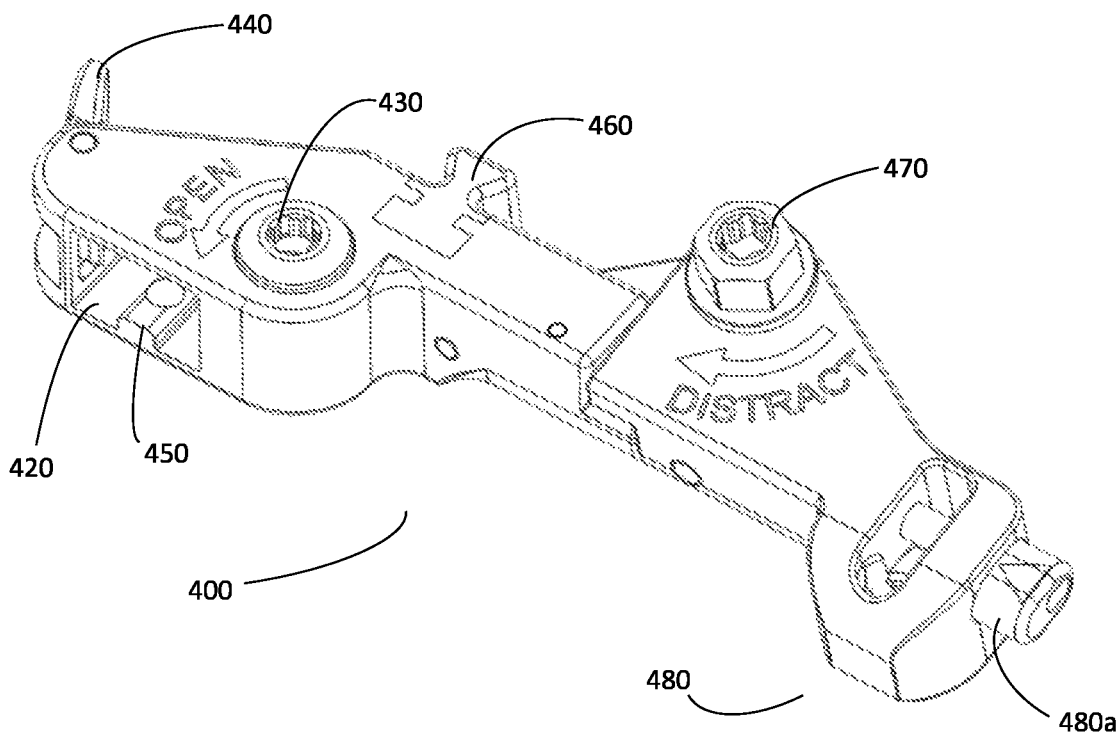
FIG. 5 is a perspective view of a second retractor arm, which is a component of the surgical retractor shown in FIG. 1.

FIG. 5 is a perspective view of retractor arm 400 without base portion 100 or retractor blade 410. This view clearly illustrates receiving portion 420, which, in this illustrated embodiment, includes a raised or keyed portion 450 that mates with a corresponding channel on the underside of extension 110b (not illustrated) to ensure a solid engagement between retractor arm 400 and extension 110b.

Figure 17:
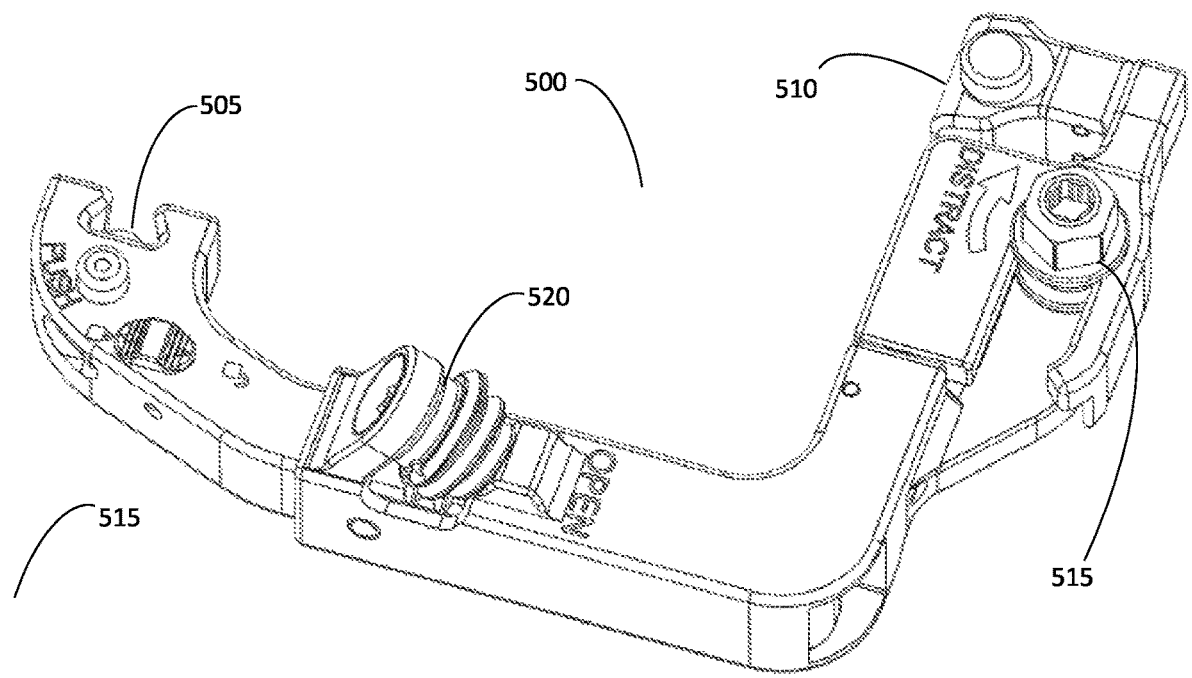
FIG. 17 is a perspective view of a lateral retractor arm that may be used with the surgical retractor shown in FIG. 1.

Retractor arm 400 also includes auxiliary attachment portion 460 that is configured to serve as a point of attachment for an auxiliary or lateral retractor arm, which is the mirror image of the embodiment shown in FIG. 17.

Retractor arm 400 further includes a distraction mechanism 470 that, when rotated, toes out the distal end of retractor blade 410, thereby allowing for or causing distraction of the vertebrae to which retractor 1000 is attached or anchored.

At its distal end, retractor arm 400 includes a retractor blade engagement portion 480 that is configured to releasably secure a proximal end of retractor blade 410. Retractor blade engagement portion 480 includes a release button 480a that when depressed, allows the proximal end of retractor blade 410 to be released from retractor blade engagement portion 480. However, engaging retractor blade 410 with retractor blade engagement portion 480 does not require the depression of button 480a because the mechanism is a passive mechanism that allows for the easy attachment of retractor blade 410 with minimal effort.

Figure 6:
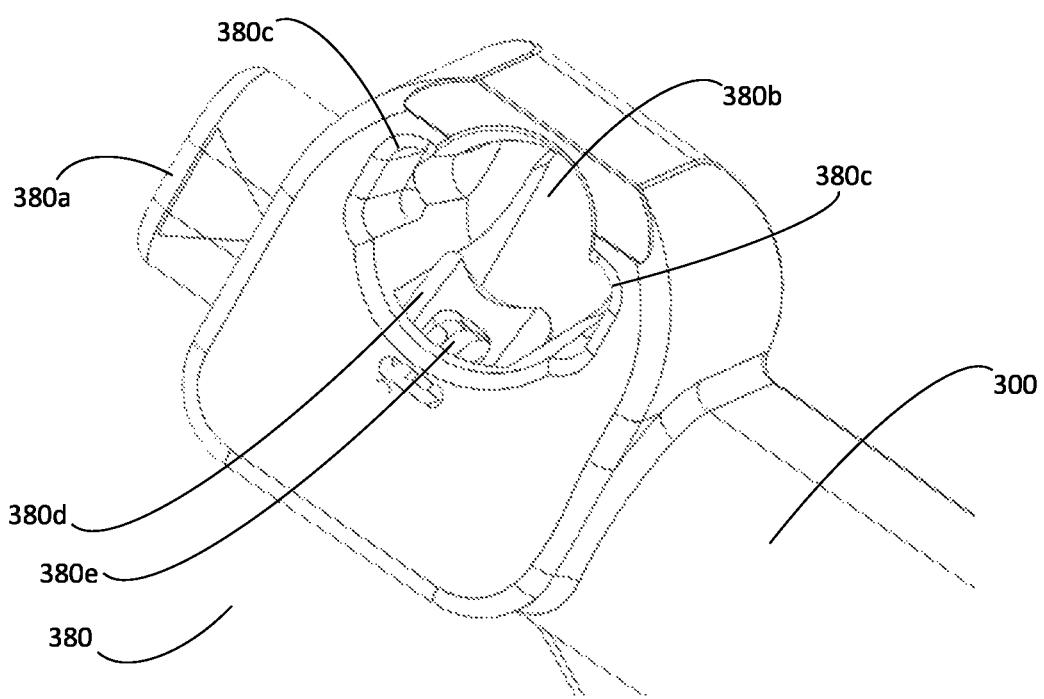
FIG. 6 is an enlarged view of the underside of a portion of the first retractor arm shown in FIG. 4.

FIG. 6 is an enlarged view of the underside of engagement portion 380 of retractor arm 300. This view illustrates that engagement portion 380 includes, in addition to release button 380a, a receiving area 380b that includes slots 380c. Within receiving area 380b is a locking mechanism 380d that is releasably held in a locked position by biasing element 380e. Although not illustrated, release button 380a includes a cut out portion that, when release button 380a is depressed, aligns with locking mechanism 380 allowing it to pivot to an unlocked position.

Figure 7:
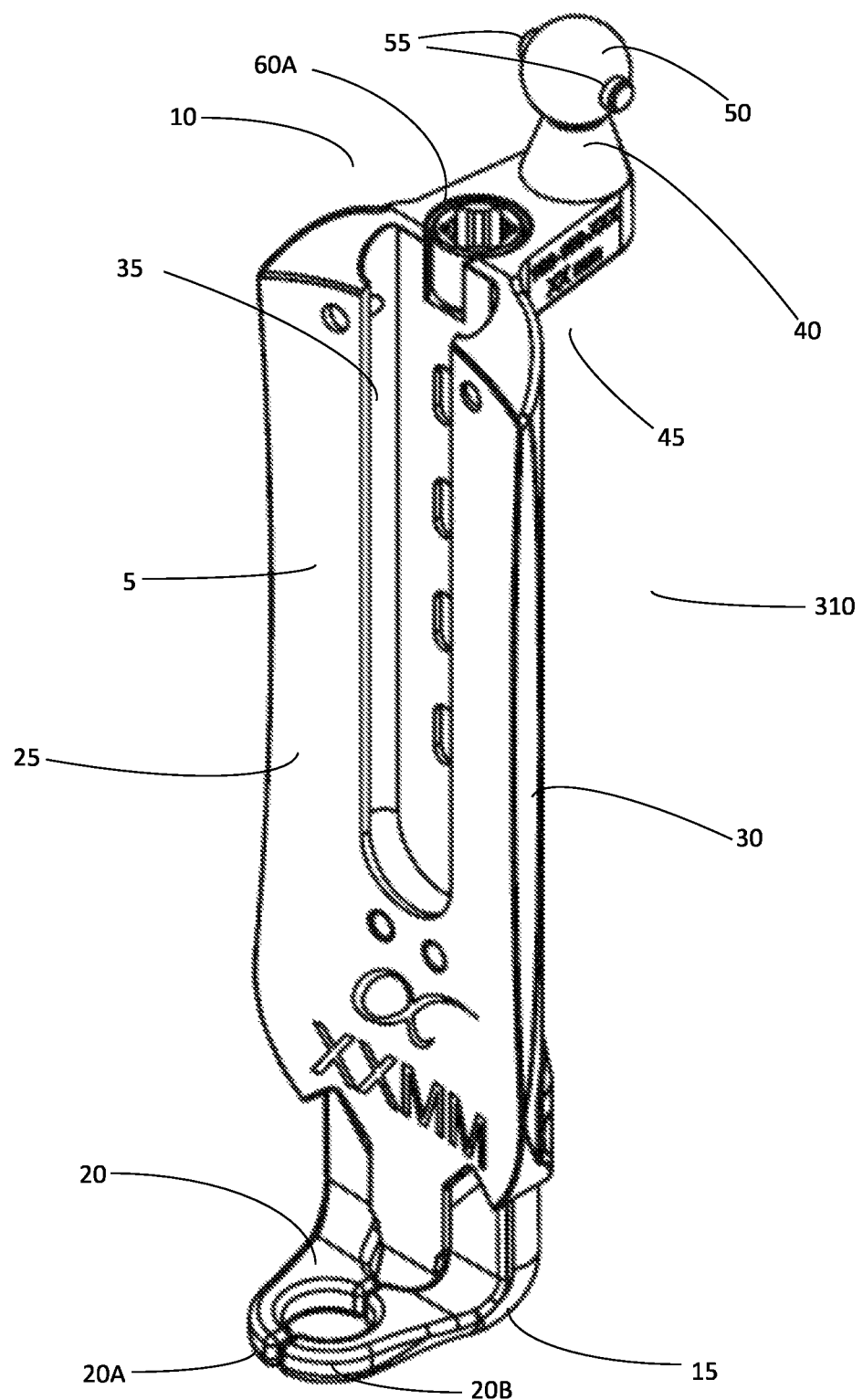
FIG. 7 is a perspective view of an anchored blade for use with a retractor assembly according to the present disclosure.

FIG. 7 is a perspective view of retractor blade 310, though the illustrated embodiment of retractor blade 410 is substantially identical. Thus, this discussion of retractor blade 310 applies equally to retractor blade 410. Similarly, the manner in which retractor blade 310 engages with retractor arm 300 is substantially identical to the manner in which retractor blade 410 engages with retractor arm 400.

FIG. 7 illustrates one such embodiment of an anchored retractor blade 310 defined as an elongate blade portion 5 having a proximal end 10 and a distal end 15. Located at the distal end 15 of blade portion 5 is an anchor assembly 20 that includes two jaw members 20A, 20B configured to be secured onto a bone implant (not illustrated), such as a pedicle screw. Jaw members 20A, 20B may be "mirrored" components, or they may each have a distinct design to facilitate attachment to a suitable anchor. Blade portion 5 has both a front face 25 and an opposing rear face 30. Visible in FIG. 7 is the fact that in this embodiment, blade portion 5 is slightly curved such that the lateral sides of blade portion 5 are curved toward front face 25.

Positioned on front face 5 is a channel 35 that extends from proximal end 10 toward distal end 15. Channel 35 is configured to facilitate the passage of instrumentation from proximal end 10 down toward distal end 15. Such instrumentation may include lighting strips used to facilitate visualization of the surgical corridor created by anchored blade 310. Along channel 35 are a number of depressions that may serve as points of fixation for the instrumentation so as to secure the instrumentation at various depths along blade portion 5. These channels may also facilitate cleaning of anchored blade 310.

Proximal end 10 of blade portion 5 includes a retractor engagement portion 40 that includes a substantially horizontal member 45 and a spherical head portion 50 with a pair of lateral extensions 55. Engagement portion 40 is configured for releasable engagement with a retractor assembly, such as retractor 1000. Spherical head portion 50 in conjunction with lateral extensions 55 are configured to allow anchored blade 310—when engaged with or secured to a retractor assembly—to be rotated to a desirable position along a single plane of rotation with lateral extensions creating the axis of rotation.

Also visible in FIG. 7 is a tool engagement portion 60A that is part of a control assembly 60 that will be discussed in greater detail with reference to FIGS. 9 and 10.

FIG. 8A illustrates anchor assembly 20 in a closed configuration, and FIG. 8B illustrates anchor assembly 20 in an open configuration. FIGS. 8A and 8B further illustrate that first jaw member 20A pivots about a first axis 65A and that second jaw member 20B pivots about a second axis 65B. In this illustrated embodiment, first axis 65A and second axis 65B lie in substantially the same plane as elongate blade portion 5 or at least in a plane parallel to the plane of elongate blade portion 5. However, despite lying in the same plane as each other, first axis 65A and second axis 65B transect each other at an angle 65C.

Angle 65C can be any suitable angle such as about 60° to about 70°, about 65° to about 75°, about 70° to about 80°, about 75° to about 85°, about 80° to about 90°, about 85° to about 95°, about 90° to about 100°, about 95° to about 105°, about 100° to about 110°, about 65° to about 105°, or about 75° to about 95°. It should be appreciated that the opening of anchoring assembly 20 should, in some embodiments, allow for easy anchoring onto and/or removal from a bone implant all while operating within the limited confines of the surgical corridor. Thus, in some embodiments, angle 65C is selected so as to not only open or close anchoring assembly 20 around a portion of the bone implant but also to facilitate the upward or downward movement of anchored blade 310 as it is either lowered into or taken out of the surgical corridor.

Angle 65C is illustrated as having its midpoint substantially in line with the center of elongate blade portion 5. This means that first axis 65A and second axis 65B are substantially symmetrical. However, in some embodiments, the two axes are not symmetrical such that the midpoint of angle 65C is not in line with the center of elongate blade portion 5. In such embodiments, it may be desirable to have first and second jaw members open and close in a non-symmetrical manner or to have one jaw member move in a more vertical line or a more horizontal line, as the case may be. For example, in some embodiments the midpoint of angle 65C is about 1° to about 4°, about 3° to about 6°, about 5° to about 8°, about 7° to about 10°, about 9° to about 12°, about 11° to about 14°, about 13° to about 16° away from the center of elongate blade portion 5.

Anchoring assembly 20 is illustrated as including first jaw member 20A and second jaw member 20B that may move in concert with each other; however, in some embodiments, only one jaw member may pivot while the other jaw member remains in the closed configuration. In some embodiments, control assembly 60 (discussed in greater detail below) proactively engages both jaw members equally when in the closed configuration while achieving the open configuration by allowing each jaw member to pivot freely, such that first and second jaw members 20A, 20B may or may not pivot in concert.

Figure 9:
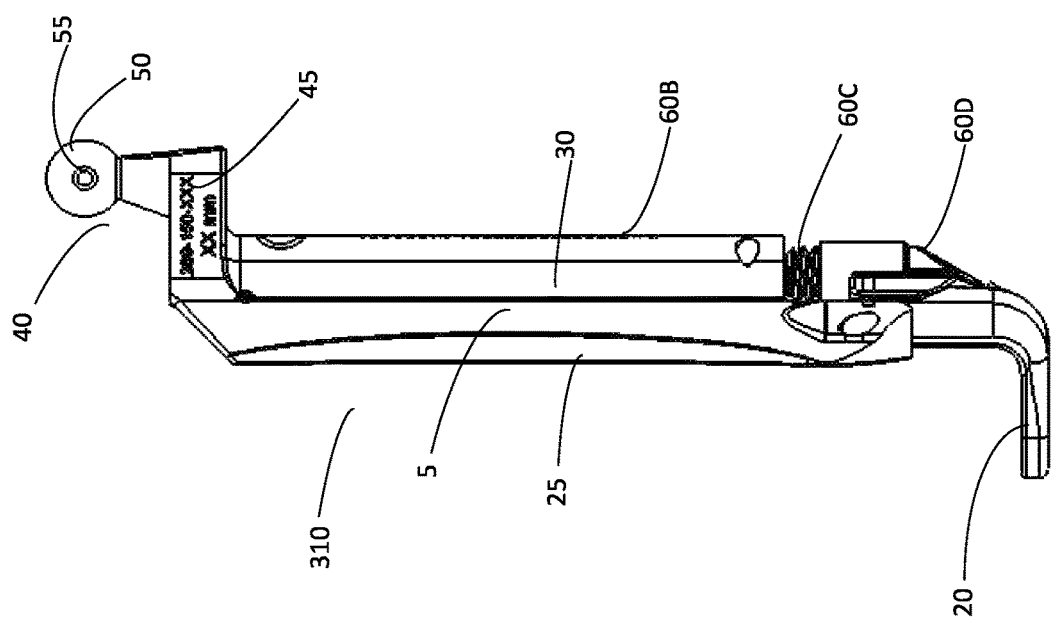
FIG. 9 is a side view of the anchored blade of FIG. 7.

FIG. 9 is a side view of anchored blade 310 illustrating a number of features such as the substantially orthogonal orientation of anchoring assembly 20 relative to elongate blade portion 5—when in the closed configuration—as well as the orthogonal orientation of elongate blade portion 5 relative to horizontal member 45 of retractor engagement portion 40. In this illustrated embodiment, elongate blade portion 5 can be said to define a first plane, a portion of anchoring assembly 20 can be said to define a second plane, and horizontal member 45 can be said to define a third plane. In some embodiments, the second and third planes are substantially parallel to each other and substantially orthogonal to the first plane—when anchoring assembly 20 is in the closed configuration. In some embodiments, one of the second plane and the third plane is substantial orthogonal to the first plane but the second and third planes are not parallel to each other. In some embodiments, neither the second plane nor the third plane is orthogonal to the first plane, and they may or may not be parallel to each other. FIG. 9 further illustrates that at least a portion of anchoring assembly 20—when in the closed configuration—lies substantially in the first plane or in a plane parallel to the first plane. This portion of anchoring assembly may be referred to as the base portion of both the first and second jaw members.

In some embodiments, the first and second planes transect each other at an angle of about 70° to about 85°, about 80° to about 95°, about 90° to about 105°, about 100° to about 115°, about 70° to about 115°, about 80° to about 100°, or about 85° to about 95°. In some embodiments, the first and third planes transect each other at an angle of about 70° to about 85°, about 80° to about 95°, about 90° to about 105°, about 100° to about 115°, about 70° to about 115°, about 80° to about 100°, or about 85° to about 95°.

FIG. 9 illustrates front face 25 and rear face 30 of elongate blade portion 5 and the fact that positioned on rear face 30 is a control assembly 60, which mechanism includes tool engagement portion 60A (illustrated in FIGS. 7 and 11), a connection rod 60C contained within connection rod housing 60B, and a movable block 60D. In this embodiment, rotation of tool engagement portion 60A rotates connection rod 60C, which in turn causes movable block 60D to translate distally or proximally. In some embodiments, control assembly is located on front face 25, such as in channel 35.

Figure 10A:
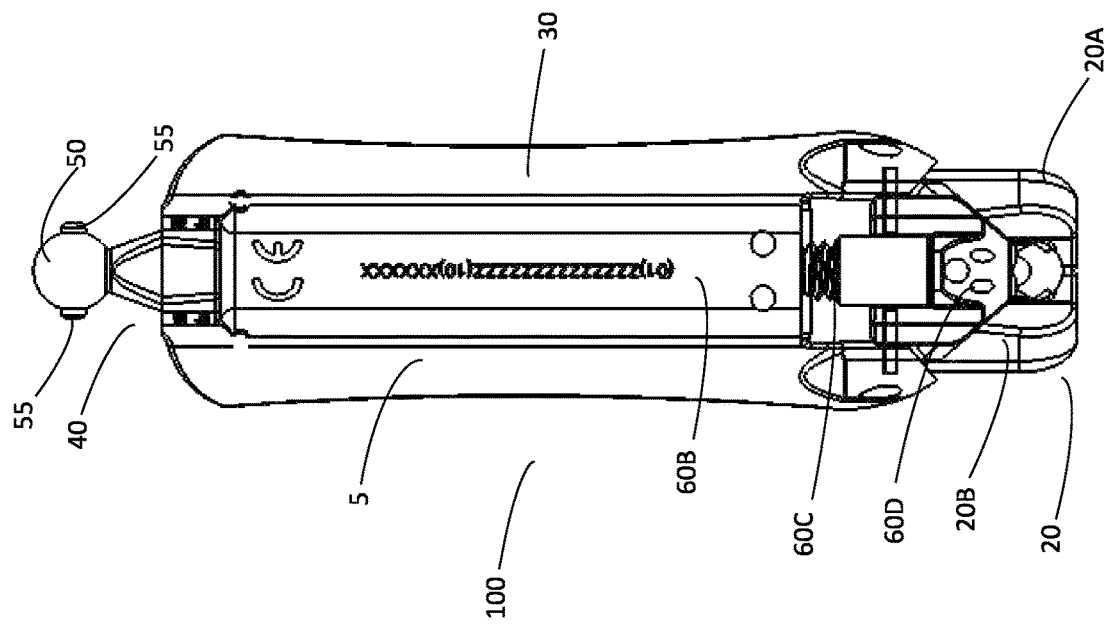
FIGS. 10A and 10B are rear plan views of the anchored blade of FIG. 7.
Figure 10B:
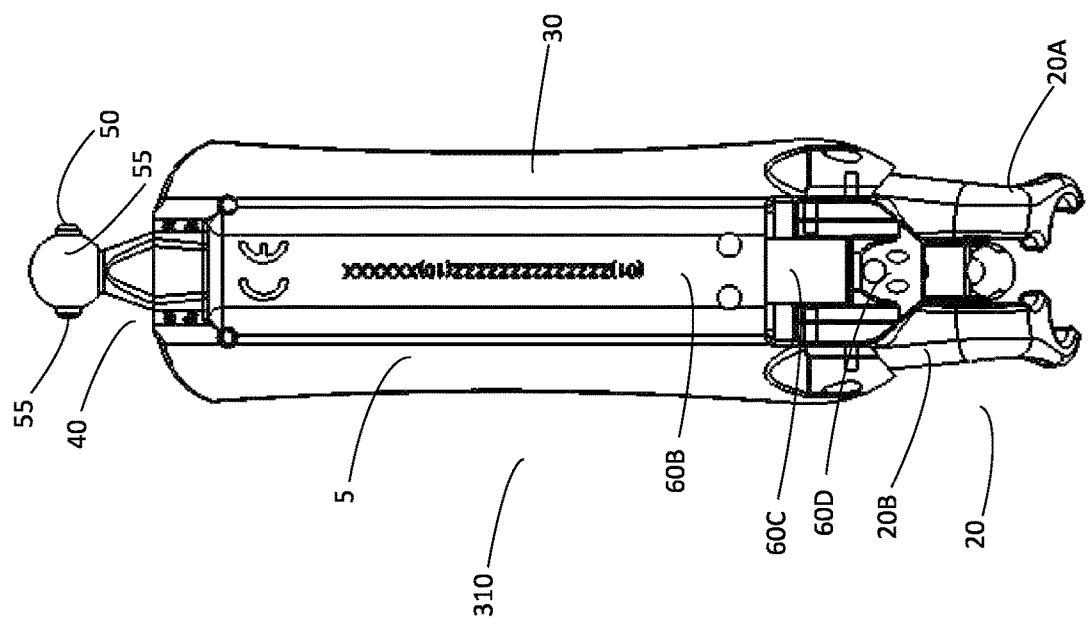

Referring now to FIGS. 10A and 10B, distal translation of movable block 60D pushes distally or downward against first and second jaw members 20A, 20B of anchor assembly 20, thereby causing first and second jaw members 20A, 20B to pivot into and be maintained in the closed configuration as illustrated in FIG. 10A. The open configuration is achieved by proximally translating movable block 60D (which is caused by rotating tool engagement portion 60D), as illustrated in FIG. 10B. When movable clock 60D translates proximally, the pressure applied to first and second jaw members 20A, 20B is reduced and removed; however, the jaw members may not automatically transition out of the closed configuration. In other words, first and second jaw members 20A, 20B may remain in the closed configuration passively. If anchoring assembly 20 is anchored to a bone implant, opening of first and second jaw members 20A, 20B may require anchored blade 310 to be pulled proximally to disengage anchoring assembly 20 from the bone implant. However, if anchoring assembly 20 is not anchored to a bone implant and there is no tissue or other object touching it, translating moveable block 60D will allow first and second jaw members to be pulled by gravity downward or distally to achieve the open configuration.

In some embodiments, distal translation of moveable block 60D causes anchoring assembly 20 to transition to the open configuration automatically without any need to move anchored blade 310. In some embodiments, either first jaw member 20A or second jaw member 20B is mechanically engaged with moveable block 60D such that proximal translation of moveable block 60D causes the relevant jaw member to transition into the open configuration while the other jaw member remains passively in the closed configuration.

In the illustrated embodiment, connection rod 60C that mechanically communicates rotation of tool engagement portion 60A to translation of moveable block 60D is contained within connection rod housing 60B. In some embodiments, connection rod 60C is not contained within a housing. In some embodiments, connection rod 60C is shorter such that tool engagement portion 60D is not located on or near retractor engagement portion 40. For example, tool engagement portion 60A may be located more distally along rear face 30 of elongate blade portion 5. Some embodiments do not include connection rod 60C at all such that tool engagement portion 60D is directly connected to block 60D.

In some embodiments, some or all of control assembly 60 is positioned on front face 25 of elongate blade portion 5. In some such embodiments, it may be desirable to maintain as much working space as possible toward the proximal end of anchored blade 310. Accordingly, control assembly 60 may lack any connection rod, such that tool engagement portion 60A is positioned just above or proximal to moveable block 60D, and an adjustment tool must extend down the length of elongate blade portion 5 along front face 25 to engage and rotate tool engagement portion 60A.

FIGS. 9 and 10 also illustrate lateral projections 55 on spherical head portion 40 of retractor engagement portion 40. In this illustrated embodiment, lateral projections 55 define an axis that produces rotation of anchored blade 310 in a plane of rotation that is roughly orthogonal to the plane defined by elongate blade portion 5. However, in some embodiments, a rotation in a different plane may be desired, in which case lateral projections 55 can be positioned accordingly on spherical head portion 40 to achieve rotation in the desired plane. Additionally, in some embodiments, lateral projections 55 are removed altogether to allow anchored blade 310 to rotate in multiple planes.

Figure 11:
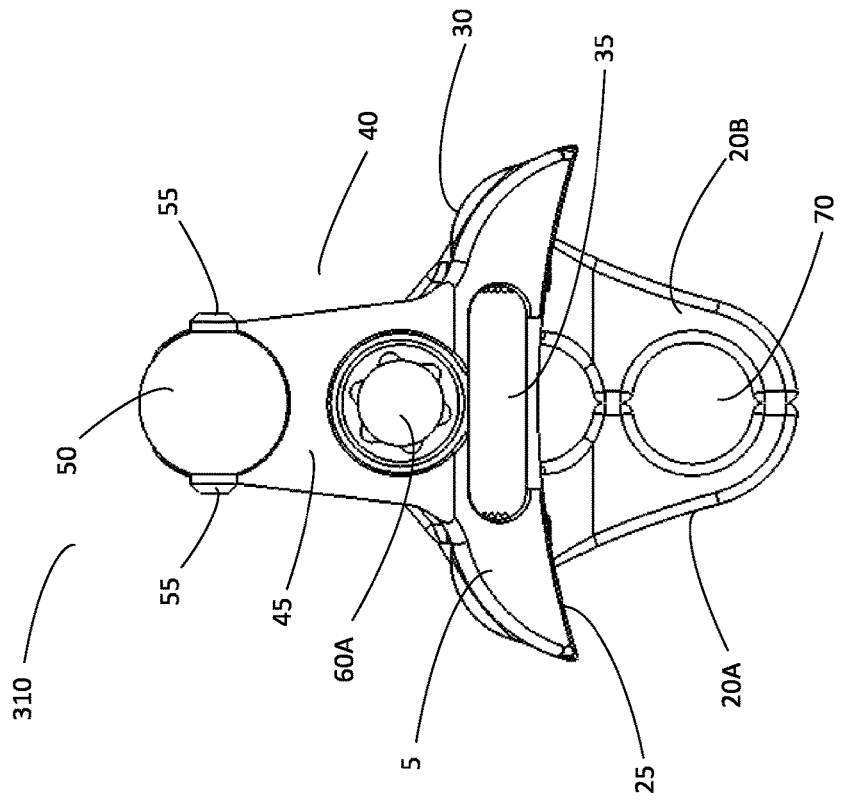
FIG. 11 is top view of the proximal end of the anchored blade of FIG. 7.

FIG. 11 is a top view of the proximal end of anchored blade 310. This perspective illustrates the structural relationships of many of the elements of anchored blade 310 as discussed above with respect to the other figures; however, FIG. 11 further illustrates the distal or arcuate portions of first and second jaw members 20A, 20B. When abutting each other in the closed configuration, first and second jaw members 20A, 20B form an opening 70 configured to anchor onto and retain a portion of a bone implant, such as a bone screw or a pedicle screw. In this illustrated embodiment, opening 70 is substantially circular; however, in some embodiments, opening 70 has other shapes, such as an oval, a square, a rectangle, etc. In this illustrated embodiment, the circular shape of opening 70 is achieved by the two half-circle aspects of first and second jaw members 20A, 20B. In some embodiments, one or both of first and second jaw members form less than two half circles. In the illustrated embodiment, the two half circles of first and second jaw members 20A, 20B are shown as substantially abutting each other at each end of the half circle. Such a configuration may not only provide greater stability or engagement for anchored blade 310 but also may provide greater tactile response for a user who engages anchored blade 310 with a bone implant. However, in some embodiments, only one end of one half circle (or other suitable shape) abuts the corresponding end of the other half circle (or other suitable shape). In some embodiments, neither end of the half circle (or other suitable shape) abuts the corresponding end of the other half circle (or other suitable shape).

The shape of opening 70 may be determined by the shape of the portion of the bone implant to which anchoring assembly 20 is to be anchored. For example, where the bone implant is a pedicle screw and the portion to be anchored to is a partially or fully spherical head, opening 70 is ideally circular in shape, and the edges of the arcuate arms of first and second jaw members 20A, 20B may further include sloped or rounded surface to accommodate or engage the spherical head of the pedicle screw. In some embodiments, the shape and side of opening 70 may be configured for attachment to the shank portion of a pedicle screw so as to allow the upper or head portion of the pedicle screw to be accessible for assembly of a tulip onto the head wherein the pedicle screw is a modular pedicle screw.

In some embodiments, the closed configuration of anchoring assembly 20 is understood to be achieved when at least a portion of first jaw member 20A is brought into and maintained in contact with at least a portion of second jaw member 20B. In some embodiments, the closed configuration is understood to be achieved when moveable block 60D is translated distally far enough to apply a force to first and second jaw members 20A, 20B to allow anchoring assembly 20 to be engaged with and anchored onto a bone implant or other suitable anchoring point even if no portion of first jaw member 20A is in contact with any portion of second jaw member 20B.

In some embodiments, the open configuration of anchoring assembly 20 is understood to be achieved when moveable block 60D is translated proximally far enough to allow first and second jaw members 20A, 20B of anchoring assembly 20 to open thereby allowing a portion of a bone implant (or other suitable anchoring point) to pass in or out of opening 70

The anchored retractor blades disclosed herein are configured for use with retractor assemblies, such as retractor 1000. Such assemblies may have one or more retractor arms, each arm configured to have attached to it (releasably or in a non-releasable manner) a retractor blade, at least one of which blades will be an anchored retractor blade according to the present disclosure. In some embodiments of retractor assemblies, two anchored blades are positioned opposite each other in the retractor assembly. Some embodiments include a medial and/or lateral blade positioned to the side of the space created by the two opposite anchored blades.

Suitable retractor assemblies may also include a support engagement portion so that the retractor assembly may be releasably secured to and held in a fixed position and orientation relative to a surgical bed. Such configurations may utilize an A-arm to secure the retractor assembly to the surgical bed.

The anchored retractor blades discussed herein can be used in methods of anchoring a surgical retractor to a bone implant or other suitable anchor. Such methods may include positioning a first anchored blade according to this disclosure within a surgical corridor so that at least a portion of the first and second jaws of the anchored blade is positioned below a top surface of a first bone implant. Once in position, a user activates the control assembly of the first anchored blade to transition the first and second jaws from the open configuration to the closed configuration to anchor the first anchored blade to the first bone implant. Some methods further include positioning a second anchored blade according to this disclosure within the surgical corridor so that at least a portion of the first and second jaws of the second anchored blade is positioned below a top surface of a second bone implant. Once in position, the user activates the control assembly of the second anchored blade to transition the first and second jaws from the open configuration to the closed configuration to anchor the second anchored blade to the second bone implant.

The above methods illustrate how the anchored blades can be secured to bone implants that have already been placed at or near the surgical site. In alternative embodiments, one or both anchored blades are secured to the bone anchors prior to the resulting construct being inserted into a patient's body near the surgical site. In such configurations, the blade/implant combination is advanced toward the surgical or anchor site and, when properly positioned, the bone implant (e.g., a pedicle screw) is advanced into bone thereby securing the anchored blade in place as well. The same steps may be followed for the other anchored blade, and with both anchored blades in position, they may be secured to a retractor assembly to establish a stable surgical corridor. In some embodiments, a driver is secured to the blade/implant combination to achieve a blade/implant/driver combination that is then advanced toward the surgical or anchor site, such that when the combination is positioned properly, the driver can be used immediately to advance the implant into bone without requiring any additional instruments or steps.

When the bone implant is a modular pedicle screw, some methods further include the step of installing a tulip on the head portion of the pedicle screw. Some methods that utilize an anchored retractor blade as disclosed herein will be part of a procedure for transforaminal lumbar interbody fixation. Some methods will be part of a procedure for a posterior lumbar interbody fixation. Some methods will be part of a procedure for a lateral lumbar interbody fixation.

Figure 12:
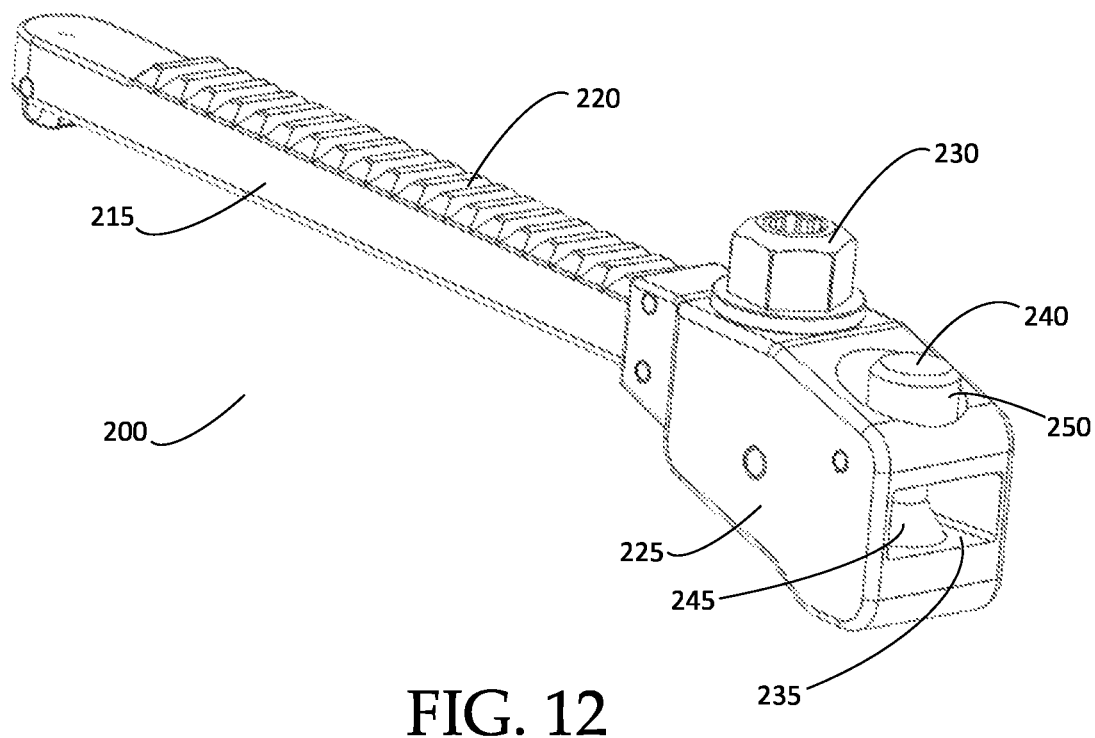
FIG. 12 is a perspective view of a medial retractor arm, which is a component of the surgical retractor shown in FIG. 1.

FIG. 12 illustrates medial retractor arm 200, which includes an elongate portion 215 having a top surface comprised of linear gear teeth 220 configured to mate with adjustment mechanism 140. As discussed above, rotation of adjustment mechanism 140 causes medial retractor arm 200 to translate linearly relative to base portion 100 as to expand or contract a medial portion of the surgical corridor created by the two or more retractor blades/arms. Medial retractor arm 200 includes at its distal end a medial blade engagement portion 225 that is pivotable relative to elongate portion 215 by virtue of a distraction mechanism 230 that, when rotated, causes engagement portion 225 to pivot downward, which means below a plane defined by elongate portion 215. Such pivoting may be useful to enlarge surgical access and/or combat tissue creep into the surgical corridor.

Engagement portion 225 includes a receiving window 235 configured to receive an engagement extension of medial retractor blade 210, which is discussed in greater detail below with respect to FIGS. 15 and 16. Engagement portion 225 further includes a release/locking mechanism 240 comprising a locking portion 245 (discussed in greater detail below with respect to FIGS. 13 and 14) and a button portion 250 that, in this illustrated embodiment, extends above a top surface of engagement portion 225.

Figure 13:
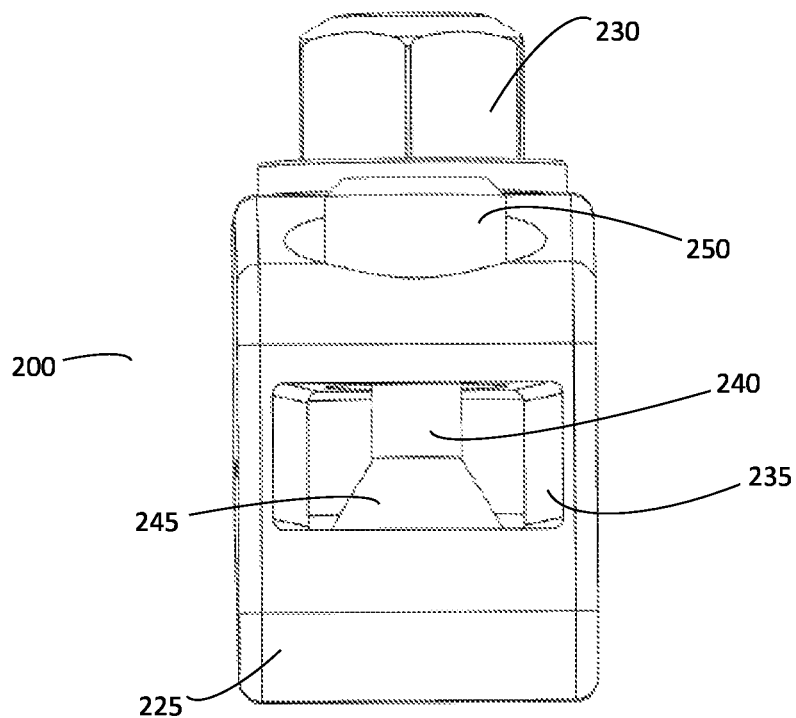
FIG. 13 is an elevation view of the distal end of the medial retractor arm shown in FIG. 12.

FIG. 13 is an elevation view of engagement portion 225 in which is visible distraction mechanism 230, receiving window 235, and release/locking mechanism 240. Not illustrated is a biasing element, such as a spring, located beneath release/locking mechanism 240 that maintains release/locking mechanism in a locked position, which is achieved when the majority of the frustoconical section of locking portion 245 is visible through receiving window 235. Pressing down on button portion 250 compresses the biasing element and allows locking portion 245 to drop below receiving window 235 so as to release the medial blade engagement portion.

Figure 14:
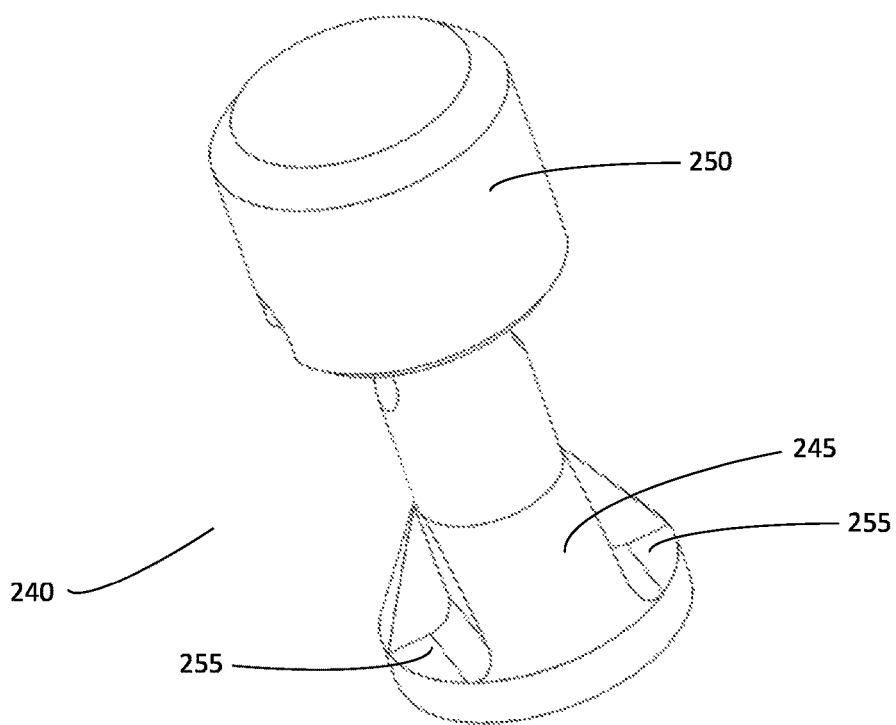
FIG. 14 is a perspective view of one element of the locking member of the medial retractor arm shown in FIG. 12.

FIG. 14 illustrates release/locking mechanism 240 in isolation and highlights the rear sections that include behind the frustoconical section two cutouts 255 configured to receive at least a portion of the medial blade engagement portion as discussed below. Some embodiments include only a single cutout 255. Some embodiments include cutouts of different shapes, though generally the shape of the cutout corresponds to the shape of an extension of the medial blade engagement portion.

Figure 15:
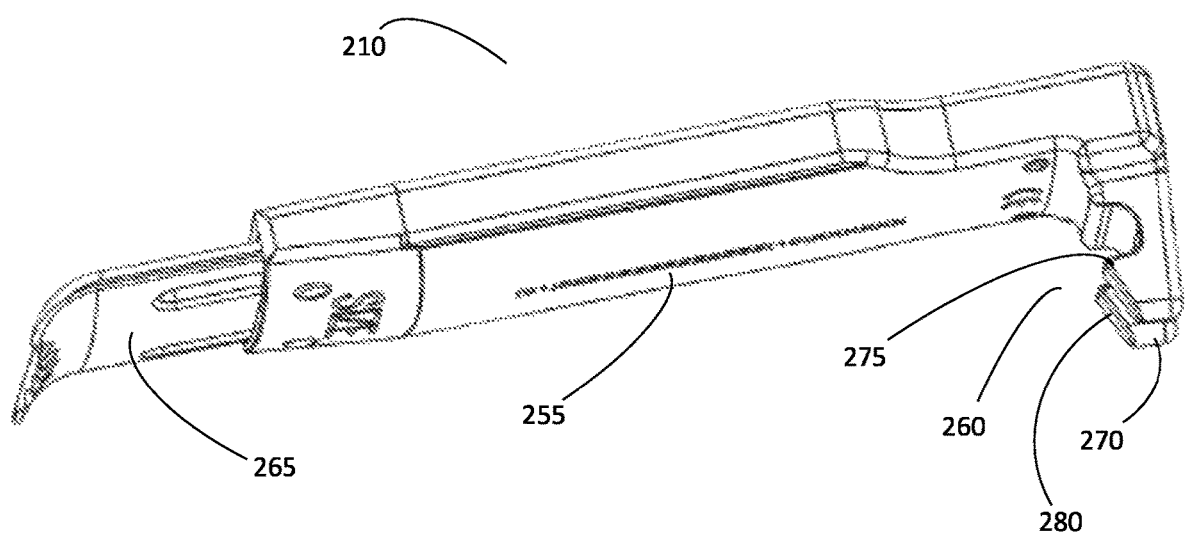
FIG. 15 is a perspective view of a medial retractor blade that may be used with the medial retractor arm shown in FIG. 12.

FIG. 15 is a perspective view of medial retractor blade 210 illustrating that it includes at its proximal end an engagement portion 260 and at its distal end an extendable portion 265. Between the proximal and distal ends is a blade body 255. Extendable portion 265 is illustrated as having, at its distal end, a curved tip. This configuration may allow medial retractor blade 210 to better retain or hold back tissue from the surgical corridor created by two or more retractor blades secured to surgical retractor 1000. Extendable portion 265 may be translated into or out of blade body 255 depending on the depth of the surgical corridor and the needs of the surgical procedure.

Engagement portion 260 includes an extension or, as is illustrated, a pair of extensions 270 configured to engage release/locking mechanism 240 when extensions 270 are inserted into receiving window 235. FIG. 15 illustrates that in this embodiment of extensions 270, they have a hook or arch 275 to them. This structural feature is configured to accommodate the frustoconical shape of locking portion 245 of release/locking mechanism 240. The sloped surfaces 280 that are adjacent to arched area 275 are configured to press down on locking portion 245 as engagement portion 260 is pressed into receiving window 235, thereby pressing down on locking portion 245, compressing the biasing element beneath it and allowing extensions 270 to at least partially pass over locking portion 245. When extensions 270 are sufficiently inserted into engagement portion 225 of medial retractor arm 200, arched area 275 allows release/locking mechanism 240 to move back into the locked position by accommodating locking portion 245 in arched area 275. Furthermore, the generally rectangular outer shape of extensions 270 correspond to the generally rectangular inner surface of receiving window 235, thereby resisting rotational movement of engagement portion and, by association, rotational movement of medial retractor blade 210.

The above-explained features are designed to allow for the passive locking of medial blade 210 with medial arm 200 without requiring any active locking steps, the activation of any other components, depressing any components or buttons, etc.

Disengaging medial retractor blade 210 from medial retractor arm 200 is achieved by depressing button portion 250, which moves locking portion 245 downward allowing extensions 270 to be pulled past lacking portion 245 and out of receiving window 235.

Figure 16:
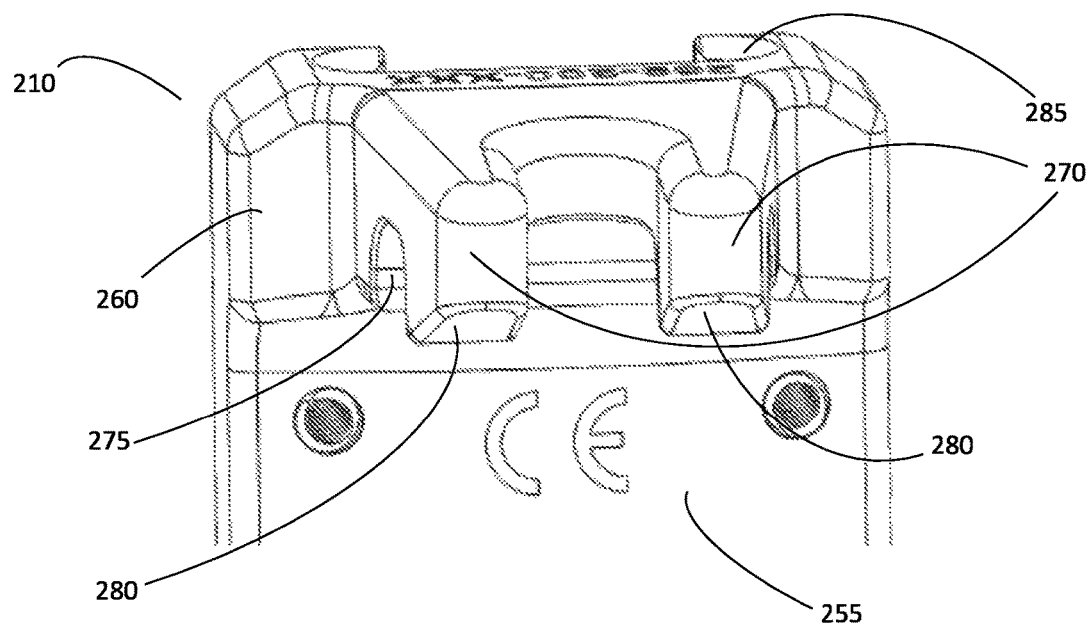
FIG. 16 is an enlarged view of the proximal end of the medial retractor blade shown in FIG. 15.

FIG. 16 further illustrates that medial retractor blade 210 may include a channel 285 that, in this embodiment, is configured to operate in a similar manner to channel 35 of anchored retractor blade 310 and/or 410.

FIG. 17 illustrates an auxiliary or lateral retractor arm 500. This illustrated lateral retractor arm 500 is configured for attachment to retractor arm 300; however, in some embodiments, lateral retractor arm 500 may be configured for attachment to retractor arm 400. This is achieved by simply reversing the orientation of the various features of lateral retractor arm 500 discussed below.

Lateral retractor arm 500 includes at its proximal end an arm engagement portion 505 and at its distal end a lateral blade engagement portion 510. Between the distal and proximal ends is a distraction mechanism 515 as well as a lateral adjustment mechanism 520, which in this illustrated embodiment comprises a worm gear. Rotation of adjustment mechanism 520 causes expansion or contraction of lateral retractor arm 500, which when attached to retractor 1000, enlarges or diminishes the size of the surgical corridor. Distraction mechanism 515, when rotated, toes out or angles a lateral retractor blade secured to lateral blade engagement portion 510. The lateral blade (not shown) may be similar in design to medial retractor blade 210. Lateral blade engagement portion 510, in this illustrated embodiment, operates similarly to medial blade engagement portion 225 in that it releasably secures a retractor blade preventing it from twisting or rotating.

To achieve a suitable surgical corridor, the surgical retractor disclosed herein may include as few as two retractor blades and as many as three retractor blades using any combination of two anchored retractor blades, one medial retractor blade, and one lateral retractor blade with the lateral retractor blade secured via a lateral retractor arm to either of the two retractor arms. For example, some configurations will include only the two anchored retractor blades opposite each other. Some configurations will include the two retractor blades and only the medial retractor blade with some of these configurations further including the lateral retractor blade attached via the lateral retractor arm to either of the two retractor arms. Some embodiments will include just one anchored retractor blade with the medial retractor arm or the lateral retractor or both the medial retractor blade and the lateral retractor blade.

EMBODIMENTS

The following embodiments are provided as examples only of specific configurations, materials, arrangements, etc. contemplated by the authors of this disclosure:

Embodiment 1. A surgical retractor comprising:
 a base portion comprising first and second extensions, a first receiving area, and one or more engagement portions;
 a medial retractor arm with proximal and distal ends, the medial retractor arm having a second receiving area at the distal end configured to releasably engage a portion of a medial retractor blade, the proximal end configured to be slidably received in the first receiving area of the base portion;
 a first retractor arm with proximal and distal ends, the first retractor arm having a third receiving area at the proximal end configured to slidably receive the first extension of the base portion and a fourth receiving area at the distal end configured to releasably engage a portion of a first retractor blade; and
 a second retractor arm with proximal and distal ends, the second retractor arm having a fifth receiving area at the proximal end configured to slidably receive the second extension of the base portion and a sixth receiving area at the distal end configured to releasably engage a portion of a second retractor blade;
 wherein the medial, first, and second retractor blades together create an adjustable surgical corridor.

Embodiment 2. The surgical retractor of Embodiment 1, wherein one or both of the first and second retractor arms further comprises a lateral arm engagement portion.

Embodiment 3. The surgical retractor of Embodiment 2, further comprising a lateral retractor arm having a proximal end and a distal end, the proximal end comprising a seventh receiving area configured to releasably engage the lateral arm engagement portion of the first or second retractor arm, the distal end comprising an eighth receiving area configured to releasably engage a portion of a lateral retractor blade.

Embodiment 4. The surgical retractor of Embodiment 2 or 3, wherein at least one of the second and eighth receiving areas comprises a housing configured to receive and maintain the portion of the medial or lateral retractor blade in a fixed orientation Embodiment 5. The surgical retractor of Embodiment 2, 3, or 4, wherein at least one of the second and eighth receiving areas comprises a first passive locking mechanism configured to receive and passively lock in place the portion of the medial or lateral retractor blade.

Embodiment 6. The surgical retractor of Embodiment 5, wherein the first passive locking mechanism comprises a spring-loaded column having a frustoconical base portion having one or more cutouts facing away from the surgical corridor.

Embodiment 7. The surgical retractor of Embodiment 6, wherein the portion of the medial blade that is received by the second and/or eighth receiving areas comprises a pair of extensions being spaced apart to accommodate a width of the spring-loaded column, each extension having a distally extending projection configured to be received by each cutout of the frustoconical cone.

Embodiment 8. The surgical retractor of Embodiment 3, 4, 5, 6, or 7, wherein the lateral retractor arm further comprises a lateral adjustment mechanism positioned between the proximal and distal ends.

Embodiment 9. The surgical retractor of Embodiment 1, 2, 3, 4, 5, 6, 7, or 8, wherein the first receiving area comprises a medial adjustment mechanism configured to engage and adjust the position of the medial retractor arm.

Embodiment 10. The surgical retractor of Embodiment 8 or 9, wherein at least one of the lateral adjustment mechanism and the medial adjustment mechanism is a worm gear.

Embodiment 11. The surgical retractor of Embodiment 2, 3, 4, 5, 6, 7, 8, 9, or 10, wherein at least one of the first, second, medial, and lateral retractor arms further comprises a distraction adjustment mechanism positioned between the proximal and distal ends.

Embodiment 12. The surgical retractor of Embodiment 1, 2, 3, 4, 5, 6, 7, 8, 9, 10, or 11, wherein at least one of the fourth and sixth receiving areas comprises a housing containing a second passive locking mechanism configured to receive and passively lock in place the portion of the first or second retractor blade.

Embodiment 13. The surgical retractor of Embodiment 12, wherein the housing is configured to allow the portion of the first or second retractor blade to pivot on a plane that transects the surgical corridor.

Embodiment 14. The surgical retractor of Embodiment 12, or 13, wherein the passive locking mechanism comprises a spring-loaded blocker that is passively maintained in a first position, wherein the blocker pivots about a first axis and is configured to rotate to a second position when the portion of the first or second retractor blade is pressed into the fourth or sixth receiving area but automatically rotates back to the first position when the portion of the first or second retractor blade is advanced sufficiently into the fourth or sixth receiving area.

Embodiment 15. The surgical retractor of Embodiment 14, wherein the passive locking mechanism comprises a spring-loaded button that, when pressed, allows the blocker to rotate to a third position that releases the portion of the first or second retractor blade from the housing of the first or second retractor blade.

Embodiment 16. The surgical retractor of Embodiment 1, 2, 3, 4, 5, 6, 7, 8, 9, 10, 11, 12, 13, 14, or 15, wherein the one or more engagement portions of the base portion comprises two engagement portions.

Embodiment 17. The surgical retractor of Embodiment 1, 2, 3, 4, 5, 6, 7, 8, 9, 10, 11, 12, 13, 14, 15, or 16, wherein the portion of the first and/or second retractor blades comprises a spherical shape with two lateral projections.

Embodiment 18. The surgical retractor of Embodiment 1, 2, 3, 4, 5, 6, 7, 8, 9, 10, 11, 12, 13, 14, 15, 16, or 17, wherein at least one of the first and second retractor blades is an anchored retractor blade.

Embodiment 19. The surgical retractor of Embodiment 18, wherein the anchored retractor blade is configured to be releasably anchored to a pedicle screw.

Embodiment 20. The surgical retractor of Embodiment 19, wherein the anchored retractor blade is the anchored blade of Embodiments 32, 33, 34, 35, 36, 37, 38, 39, 40, 41, 42, 43, 44, 45, 46, 47, 48, or 49.

Embodiment 21. The surgical retractor of Embodiment 1, 2, 3, 4, 5, 6, 7, 8, 9, 10, 11, 12, 13, 14, 15, 16, 17, 18, 19, or 20, wherein at least one of the second and third receiving areas comprises a ratchet mechanism configured to lock the first or second retractor arm in position along the first or second extension as the first or second retractor arm is advanced along the first or second extension away from the medial retractor arm.

Embodiment 22. The surgical retractor of Embodiment 21, wherein the ratchet mechanism comprises a release lever that when pulled disengages the ratchet mechanism from the first or second extension to allow free movement of the first or second retractor arm along the first or second extension.

Embodiment 23. The surgical retractor of Embodiment 1, 2, 3, 4, 5, 6, 7, 8, 9, 10, 11, 12, 13, 14, 15, 16, 17, 18, 19, 20, 21, or 22, wherein at least one of the second and third receiving areas comprises an advancement mechanism that when rotated advances the first or second retractor arm along away from the medial retractor arm.

Embodiment 24. The surgical retractor of Embodiment 21, 22, or 23, wherein at least one of the first and second extensions comprises ratchet teeth positioned on a first side and a second side—opposite the first side—of the first or second extensions.

Embodiment 25. A method of using an anchored surgical retractor, the method comprising:
  inserting first and second retractor blades through an opening in a patient near the patient's spine, the first and second retractor blades each comprising:
    an elongate blade portion having a proximal end and a distal end;
    a retractor engagement portion positioned at the proximal end of the elongate blade portion;
    an anchor mechanism positioned at the distal end of the distal end of the elongate blade portion and configured to engage a bone implant, the anchor mechanism comprising a first jaw and second jaw configured to occupy a closed configuration and an open configuration, wherein, when in the open configuration, a portion of the bone implant is able to pass through the first and second jaws; and
    a control assembly configured to transition the first and second jaws between the open configuration and the closed configuration;
  advancing the first and second retractor blades toward respective first and second bone anchors each secured to the patient's spine
  positioning a portion of each of the first and second bone anchors between the respective first and second jaws of the first and second retractor blades;
  manipulating each control assembly so that each set of first and second jaws occupies and is retained in the closed position around the respective portions of the first and second bone anchors;
  releasably securing the first and second retractor blades to a surgical retractor assembly, wherein the retractor assembly comprises:
    a base portion;
    a first retractor arm that releasably receives a portion of the retractor engagement portion of the first retractor blade; and
    a second retractor arm that releasably receives a portion of the retractor engagement portion of the second retractor blade;
  manipulating one or both of the first and second retractor arms so as to create and/or enlarge a surgical corridor created between the first and second retractor blades.

Embodiment 26. The method of Embodiment 25, wherein the base portion further comprises one or more engagement portions and wherein the method further comprises securing a stabilization device to one of the one or more engagement portions of the base portion, the stabilization device being secured to a surgical table so as to fix the location of the base portion relative to the surgical table.

Embodiment 27. The method of Embodiment 26, wherein the stabilization device is an A-arm.

Embodiment 28. The method of Embodiment 25, 26, or 27, further comprising:
  inserting through the opening and advancing toward the patient's spine a medial retractor blade, the medial retractor blade comprising:
    an elongate blade portion having a proximal end and a distal end; and
    a retractor engagement portion positioned at the proximal end of the elongate blade portion;
  releasably securing the medial retractor blade to the retractor assembly, wherein the retractor assembly further comprises a medial retractor arm positioned in and opening of and moveable relative to the base portion, the medial retractor arm having at its distal end a blade engagement portion configured to releasably receive a portion of the retractor engagement portion of the medial retractor blade;
  adjusting the position of the medial retractor arm relative to the base portion so as to retain and/or enlarge the surgical corridor.

Embodiment 29. The method of Embodiment 25, 26, 27, or 28, further comprising:
  inserting through the opening and advancing toward the patient's spine a lateral retractor blade, the lateral retractor blade comprising:
    an elongate blade portion having a proximal end and a distal end; and
    a retractor engagement portion positioned at the proximal end of the elongate blade portion;
  releasably securing the lateral retractor blade to the retractor assembly, wherein the retractor assembly further comprises a lateral retractor arm releasably secured to either the first or second retractor arm, the lateral retractor arm having at its distal end a blade engagement portion configured to releasably receive a portion of the retractor engagement portion of the lateral retractor blade;

adjusting the position of the lateral retractor arm relative to the first or second retractor arm so as to retain and/or enlarge the surgical corridor.

Embodiment 30. The method of Embodiment 25, 26, 27, 28, 29, or 30, wherein the first and second retractor arms further comprise a distraction mechanism configured to adjust the angular orientation of the first and second retractor blades, respectively, relative to the first and second retractor arms, and wherein the method further comprises utilizing one or both distraction mechanisms—when the first and second retractor blades are respectively anchored to the first and second bone anchors each of which is secured to a distinct vertebra—to distract the vertebrae.

Embodiment 31. The method of Embodiment 25, 26, 27, 28, 29, or 30, wherein the anchored surgical retractor is the surgical retractor of any one of Embodiments 1, 2, 3, 4, 5, 6, 7, 8, 9, 10, 11, 12, 13, 14, 15, 16, 17, 18, 19, 20, 21, 22, 23, or 24.

Embodiment 32. An anchored blade for use with a surgical retractor, the blade comprising:
- an elongate blade portion having a proximal end, a distal end, a front face configured to face a surgical corridor, a rear face opposite the front face, and at least one channel extending from the proximal end toward the distal end along the front face;
- a retractor engagement portion positioned at the proximal end of the elongate blade portion;
- a first jaw and second jaw positioned at the distal end of the elongate blade portion and configured to engage a bone implant, the first and second jaws configured to occupy a closed configuration and an open configuration, wherein, when in the open configuration, a portion of the bone implant is able to pass through the first and second jaws;
- a control assembly configured to transition the first and second jaws between the open configuration and the closed configuration.

Embodiment 33. The anchored blade of Embodiment 32, wherein the elongate blade portion lies substantially in a first plane and a first portion of the first and second jaws—when in the closed configuration—lies in a second plane, the first and second planes transecting each other at an angle of about 70° to about 85°, about 80° to about 95°, about 90° to about 105°, about 100° to about 115°, about 70° to about 115°, about 80° to about 100°, or about 85° to about 95°.

Embodiment 34. The anchored blade of Embodiment 32 or 33, wherein at least a portion of the retractor engagement portion lies in a third plane, the first and third planes transecting each other at an angle of about 70° to about 85°, about 80° to about 95°, about 90° to about 105°, about 100° to about 115°, about 70° to about 115°, about 80° to about 100°, or about 85° to about 95°.

Embodiment 35. The anchored blade of Embodiment 34, wherein the second and third planes are substantially parallel.

Embodiment 36. The anchored blade of Embodiment 32, 33, 34, or 35, wherein a second portion of the first and second jaws-when in the closed configuration-lies in the first plane.

Embodiment 37. The anchored blade of Embodiment 32, 33, 34, 35, or 36, wherein the first jaw is configured to pivot about a first axis, and wherein the second jaw is configured to pivot about a second axis.

Embodiment 38. The anchored blade of Embodiment 37, wherein the first and second axes lie in the first plane and transect each other such that an angle between the first and second axes is about 60° to about 70°, about 65° to about 75°, about 70° to about 80°, about 75° to about 85°, about 80° to about 90°, about 85° to about 95°, about 90° to about 100°, about 95° to about 105°, about 100° to about 110°, about 65° to about 105°, or about 75° to about 95°.

Embodiment 39. The anchored blade of Embodiment 38, wherein the first and second axes are symmetrical relative to the elongate blade portion.

Embodiment 40. The anchored blade of Embodiment 32, 33, 34, 35, 36, 37, 38, or 39, wherein the first and/or second jaw comprises:
- a base portion configured to pivotably engage the distal end of the elongate blade portion; and
- an arcuate portion configured to engage the bone implant when the first and second jaws are in the closed configuration.

Embodiment 41. The anchored blade of Embodiment 40, wherein the arcuate portion is sized and shaped to engage a head of a pedicle screw.

Embodiment 42. The anchored blade of Embodiment 41, wherein the first and second jaws are configured to allow for the assembly of a modular tulip on the head of the pedicle screw when the first and second jaws are in the closed configuration.

Embodiment 43. The anchored blade of Embodiment 32, 33, 34, 35, 36, 37, 38, 39 40, 41, or 42, wherein the front face of the elongate blade portion comprises a curvature such that lateral sides of the front face are raised toward the surgical corridor.

Embodiment 44. The anchored blade of Embodiment 32, 33, 34, 35, 36, 37, 38, 39 40, 41, 42, or 43, wherein the control assembly is positioned on the rear face of the elongate blade portion.

Embodiment 45. The anchored blade of Embodiment 32, 33, 34, 35, 36, 37, 38, 39 40, 41, 42, 43, or 44, wherein the control assembly comprises:
- a tool engagement portion;
- a movable block configured to engage the first and second jaws so as to transition them between the open and closed configurations; and
- a connection rod mechanically connecting the tool engagement portion and the movable block and configured to translate rotation of the tool engagement portion into movement of the block either distally or proximally along the elongate blade portion.

Embodiment 46. The anchored blade of Embodiment 45, wherein the tool engagement portion is positioned at the proximal end of the elongate blade portion.

Embodiment 47. The anchored blade of Embodiment 45 or 46, wherein the movable block is configured to apply an equal force to both the first and second jaws so as to cause them to move in unison between the open and closed configurations.

Embodiment 48. The anchored blade of Embodiment 32, 33, 34, 35, 36, 37, 38, 39 40, 41, 42, 43, 44, 45, 46, or 47, wherein the retractor engagement portion comprises a spherical portion configured to be received by a retractor assembly.

Embodiment 49. The anchored blade of Embodiment 48, wherein the spherical portion has a pair of lateral extensions configured to allow the anchored blade to rotate relative to a retractor assembly in only a single plane.

Embodiment 50. A surgical retractor system comprising:
- a retractor assembly comprising a first retractor arm and a second retractor arm, each retractor arm configured to releasably engage a retractor blade;
- a support engagement portion configured to be releasably engaged with a support structure; and a first anchored blade comprising the anchored blade of Embodiment 32, 33, 34, 35, 36, 37, 38, 39 40, 41, 42, 43, 44, 45, 46, 47, 48, or 49 releasably engaged with the first retractor arm.

Embodiment 51. The surgical retractor system of Embodiment 50 further comprising a second anchored blade comprising the anchored blade of Embodiment 32, 33, 34, 35, 36, 37, 38, 39 40, 41, 42, 43, 44, 45, 46, 47, 48, or 49 releasably engaged with the second retractor arm.

Embodiment 52. The surgical retractor system of Embodiment 50 or 51, wherein the retractor assembly further comprises a medial blade engagement portion configured to releasably engage a medial retractor blade.

Embodiment 53. The surgical retractor system of Embodiment 52, further comprising a medial retractor blade releasably engaged with the medial blade engagement portion of the retractor assembly.

Embodiment 54. The surgical retractor system of Embodiment 50, 51, 52, or 53, wherein the support structure is secured to a surgical bed or a surgical frame.

Embodiment 55. The surgical retractor system of Embodiment 50, 51, 52, 53, or 54, wherein the support structure is an A-arm.

Embodiment 56. A method of securing an anchored blade to a first bone implant, the method comprising:
  positioning a first anchored blade comprising the anchored blade of Embodiment 32, 33, 34, 35, 36, 37, 38, 39 40, 41, 42, 43, 44, 45, 46, 47, 48, or 49 so that at least a portion of the first and second jaws of the anchored blade is positioned below a top surface of the first bone implant;
  activating the control assembly of the first anchored blade to transition the first and second jaws from the open configuration to the closed configuration to anchor the first anchored blade to the first bone implant.

Embodiment 57. The method of Embodiment 56 further comprising:
  positioning a second anchored blade comprising the anchored blade of Embodiment 32, 33, 34, 35, 36, 37, 38, 39 40, 41, 42, 43, 44, 45, 46, 47, 48, or 49 so that at least a portion of the first and second jaws of the second anchored blade is positioned below a top surface of a second bone implant; and
  activating the control assembly of the second anchored blade to transition the first and second jaws from the open configuration to the closed configuration to anchor the second anchored blade to the second bone implant.

Embodiment 58. The method of Embodiment 56 or 57, wherein the first bone implant is secured to a first vertebra prior to the first anchored blade is secured to the first bone implant and/or the second bone implant is secured to a second vertebra prior to the second anchored blade is secured to the second bone implant.

Embodiment 59. The method of Embodiment 56 or 57, wherein the first bone implant is secured to a first vertebra after the first anchored blade is secured to the first bone implant and/or the second bone implant is secured to a second vertebra after the second anchored blade is secured to the second bone implant.

Embodiment 60. The method of 28, wherein a driver is secured to the first bone anchor or second bone anchor prior to securing the first or second bone anchor to the first or second vertebra.

Embodiment 61. The method of Embodiment 25, 26, 27, 28, or 29, wherein the first bone implant and/or the second bone implant is a pedicle screw having a threaded shank portion and a head portion.

Embodiment 62. The method of Embodiment 30, wherein the head portion is at least partially spherical in shape.

Embodiment 63. The method of Embodiment 30 or 31, wherein the pedicle screw is a component of a modular screw assembly.

Embodiment 64. The method of Embodiment 32 further comprising assembling the modular screw assembly after the first and/or second anchored blades have been anchored to the first and/or second bone implants, respectively.

Embodiment 65. The method of Embodiment 25, 26, 27, 28, 29, 30, 31, 32, or 33, wherein the method forms part of a procedure for transforaminal lumbar interbody fixation.

Embodiment 66. An anchored surgical retractor assembly comprising:
  a base portion comprising first and second extensions and one or more engagement portions;
  a first retractor arm with proximal and distal ends, the first retractor arm having a third receiving area at the proximal end configured to slidably receive the first extension of the base portion and a fourth receiving area at the distal end configured to releasably engage a portion of a first retractor blade; and
  a second retractor arm with proximal and distal ends, the second retractor arm having a fifth receiving area at the proximal end configured to slidably receive the second extension of the base portion and a sixth receiving area at the distal end configured to releasably engage a portion of a second retractor blade;
  wherein the medial, first, and second retractor blades together create an adjustable surgical corridor; and
  wherein the first and second retractor blades comprise:
    an elongate blade portion having a proximal end and a distal end;
    a retractor engagement portion positioned at the proximal end of the elongate blade portion; and
    a first jaw and second jaw positioned at the distal end of the elongate blade portion and configured to engage a bone implant, the first and second jaws configured to occupy a closed configuration and an open configuration, wherein, when in the open configuration, a portion of the bone implant is able to pass through the first and second jaws.

Embodiment 67. The retractor assembly of Embodiment 66, wherein the first and second retractor blades further comprise a control assembly configured to transition the first and second jaws between the open configuration and the closed configuration.

Embodiment 68. The retractor assembly of Embodiment 66 or 67, wherein the base portion further comprises a first receiving area and wherein the retractor assembly further comprises a medial retractor arm with proximal and distal ends, the medial retractor arm having a second receiving area at the distal end configured to releasably engage a portion of a medial retractor blade, the proximal end configured to be slidably received in the first receiving area of the base portion.

Embodiment 69. The retractor assembly of Embodiment 66, 67, or 68, further comprising a lateral retractor arm having a proximal end and a distal end, the proximal end comprising a seventh receiving area configured to releasably engage a lateral arm engagement portion located on one of the first or second retractor arm, the distal end comprising an eighth receiving area configured to releasably engage a portion of a lateral retractor blade.

Embodiment 70. The retractor assembly of Embodiment 66, 67, 68, or 69, wherein at least one of the first and second retractor blades is the anchored blade of Embodiment 32, 33, 34, 35, 36, 37, 38, 39, 40, 41, 42, 43, 44, 45, 46, 47, 48, or 49.

Embodiment 71. The retractor assembly of Embodiment 66, 67, 68, or 69, wherein the first and second retractor blades are each the anchored blade of Embodiment 32, 33, 34, 35, 36, 37, 38, 39, 40, 41, 42, 43, 44, 45, 46, 47, 48, or 49.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It should also be noted that some of the embodiments disclosed herein may have been disclosed in relation to a particular approach (e.g., lateral or transforaminal); however, other approaches (e.g., anterior, posterior, etc.) are also contemplated.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. In one embodiment, the terms "about" and "approximately" refer to numerical parameters within 10% of the indicated range.

The terms "a," "an," "the," and similar referents used in the context of describing the embodiments of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the embodiments of the present disclosure and does not pose a limitation on the scope of the present disclosure. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the author(s) of this disclosure for carrying out the embodiments disclosed herein. Of course, variations on these described embodiments will become apparent to those of ordinary skill in the art upon reading the foregoing description. The author(s) expects skilled artisans to employ such variations as appropriate, and the author(s) intends for the embodiments of the present disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of this disclosure so claimed are inherently or expressly described and enabled herein.

Furthermore, if any references have been made to patents and printed publications throughout this disclosure, each of these references and printed publications are individually incorporated herein by reference in their entirety.

In closing, it is to be understood that the embodiments disclosed herein are illustrative of the principles of the present disclosure. Other modifications that may be employed are within the scope of this disclosure. Thus, by way of example, but not of limitation, alternative configurations of the embodiments of the present disclosure may be utilized in accordance with the teachings herein. Accordingly, the present disclosure is not limited to that precisely as shown and described.

The invention claimed is:

1. An anchored blade for use with a surgical retractor, the blade comprising:
   an elongate blade portion having a proximal end, a distal end, a front face configured to face a surgical corridor, a rear face opposite the front face, and at least one channel extending from the proximal end toward the distal end along the front face;
   a retractor engagement portion positioned at the proximal end of the elongate blade portion;
   a first jaw and second jaw positioned at the distal end of the elongate blade portion and configured to engage a bone implant, the first and second jaws configured to occupy a closed configuration and an open configuration, wherein, when in the open configuration, a portion of the bone implant is able to pass through the first and second jaws, and wherein the first jaw is configured to pivot about a first axis, and wherein the second jaw is configured to pivot about a second axis;

a control assembly configured to transition the first and second jaws between the open configuration and the closed configuration;

wherein the elongate blade portion lies substantially in a first plane and a first portion of the first and second jaws lies in a second plane, the first and second planes being substantially perpendicular to each other when in the closed configuration and not perpendicular when in the open configuration.

2. The anchored blade of claim 1, wherein a second portion of the first and second jaws—when in the closed configuration—lies in the first plane.

3. The anchored blade of claim 1, wherein the first and second axes lie in the first plane and transect each other such that an angle between the first and second axes is about 65° to about 105°.

4. The anchored blade of claim 3, wherein the first and second axes are symmetrical relative to the elongate blade portion.

5. The anchored blade of claim 1, wherein the first and/or second jaw comprises:
   a base portion configured to pivotably engage the distal end of the elongate blade portion; and
   an arcuate portion configured to engage the bone implant when the first and second jaws are in the closed configuration.

6. The anchored blade of claim 5, wherein the arcuate portion is sized and shaped to engage a head of a pedicle screw.

7. The anchored blade of claim 6, wherein the first and second jaws are configured to allow for the assembly of a modular tulip on the head of the pedicle screw when the first and second jaws are in the closed configuration.

8. The anchored blade of claim 1, wherein the front face of the elongate blade portion comprises a curvature such that lateral sides of the front face are raised toward the surgical corridor.

9. The anchored blade of claim 1, wherein the control assembly is positioned on the rear face of the elongate blade portion.

10. A surgical retractor system comprising:
   a retractor assembly comprising a first retractor arm and a second retractor arm, each retractor arm configured to releasably engage a retractor blade;
   a support engagement portion configured to be releasably engaged with a support structure; and
   a first anchored blade comprising the anchored blade of claim 1 releasably engaged with the first retractor arm.

11. The surgical retractor system of claim 10, further comprising a second anchored blade comprising the anchored blade of claim 1 releasably engaged with the second retractor arm.

12. The surgical retractor system of claim 10, wherein the retractor assembly further comprises a medial blade engagement portion configured to releasably engage a medial retractor blade.

13. An anchored blade for use with a surgical retractor, the blade comprising:
   an elongate blade portion having a proximal end, a distal end, a front face configured to face a surgical corridor, a rear face opposite the front face, and at least one channel extending from the proximal end toward the distal end along the front face;
   a retractor engagement portion positioned at the proximal end of the elongate blade portion;
   a first jaw and second jaw positioned at the distal end of the elongate blade portion and configured to engage a bone implant, the first and second jaws configured to occupy a closed configuration and an open configuration, wherein, when in the open configuration, a portion of the bone implant is able to pass through the first and second jaws;
   a control assembly configured to transition the first and second jaws between the open configuration and the closed configuration, wherein the control assembly comprises:
      a tool engagement portion;
      a movable block configured to engage the first and second jaws so as to transition them between the open and closed configurations; and
      a connection rod mechanically connecting the tool engagement portion and the movable block and configured to translate rotation of the tool engagement portion into movement of the block either distally or proximally along the elongate blade portion.

14. The anchored blade of claim 13, wherein the elongate blade portion lies substantially in a first plane and a first portion of the first and second jaws lies in a second plane, the first and second planes being substantially perpendicular to each other when in the closed configuration and not perpendicular when in the open configuration.

15. The anchored blade of claim 13, wherein the first jaw is configured to pivot about a first axis, and wherein the second jaw is configured to pivot about a second axis.

16. The anchored blade of claim 15, wherein the first and second axes lie in the first plane and transect each other such that an angle between the first and second axes is about 65° to about 105°.

17. The anchored blade of claim 16, wherein the first and second axes are symmetrical relative to the elongate blade portion.

18. The anchored blade of claim 13, wherein the movable block is configured to apply an equal force to both the first and second jaws so as to cause them to move in unison between the open and closed configurations.

19. A surgical retractor system comprising:
   a retractor assembly comprising a first retractor arm and a second retractor arm, each retractor arm configured to releasably engage a retractor blade;
   a support engagement portion configured to be releasably engaged with a support structure; and
   a first anchored blade comprising the anchored blade of claim 13 releasably engaged with the first retractor arm.

20. The surgical retractor system of claim 19, further comprising a second anchored blade comprising the anchored blade of claim 13 releasably engaged with the second retractor arm.

21. The surgical retractor system of claim 19, wherein the retractor assembly further comprises a medial blade engagement portion configured to releasably engage a medial retractor blade.

22. An anchored blade for use with a surgical retractor, the blade comprising:
   an elongate blade portion having a proximal end, a distal end, a front face configured to face a surgical corridor, a rear face opposite the front face, and at least one channel extending from the proximal end toward the distal end along the front face;

a retractor engagement portion positioned at the proximal end of the elongate blade portion, the retractor engagement portion comprises a spherical portion configured to be received by a retractor assembly, wherein the spherical portion has a pair of lateral extensions configured to allow the anchored blade to rotate relative to a retractor assembly in only a single plane;

a first jaw and second jaw positioned at the distal end of the elongate blade portion and configured to engage a bone implant, the first and second jaws configured to occupy a closed configuration and an open configuration, wherein, when in the open configuration, a portion of the bone implant is able to pass through the first and second jaws;

a control assembly configured to transition the first and second jaws between the open configuration and the closed configuration.

23. The anchored blade of claim 22, wherein the elongate blade portion lies substantially in a first plane and a first portion of the first and second jaws lies in a second plane, the first and second planes being substantially perpendicular to each other when in the closed configuration and not perpendicular when in the open configuration.

24. The anchored blade of claim 22, wherein the first jaw is configured to pivot about a first axis, and wherein the second jaw is configured to pivot about a second axis.

25. The anchored blade of claim 24, wherein the first and second axes lie in the first plane and transect each other such that an angle between the first and second axes is about 65° to about 105°.

26. The anchored blade of claim 25, wherein the first and second axes are symmetrical relative to the elongate blade portion.

27. A surgical retractor system comprising:
a retractor assembly comprising a first retractor arm and a second retractor arm, each retractor arm configured to releasably engage a retractor blade;
a support engagement portion configured to be releasably engaged with a support structure; and
a first anchored blade comprising the anchored blade of claim 22 releasably engaged with the first retractor arm.

28. The surgical retractor system of claim 27, further comprising a second anchored blade comprising the anchored blade of claim 22 releasably engaged with the second retractor arm.

29. The surgical retractor system of claim 27, wherein the retractor assembly further comprises a medial blade engagement portion configured to releasably engage a medial retractor blade.

* * * * *